United States Patent
Marshall

(10) Patent No.: US 7,215,803 B2
(45) Date of Patent: May 8, 2007

(54) METHOD AND APPARATUS FOR INTERACTIVE REMOTE VIEWING AND COLLABORATION OF DENTAL IMAGES

(75) Inventor: Michael C. Marshall, Savage, MN (US)

(73) Assignee: GeoDigm Corporation, Chanhassen, MN (US)

( * ) Notice: Subject to any disclaimer, the term of this patent is extended or adjusted under 35 U.S.C. 154(b) by 26 days.

(21) Appl. No.: 10/960,193

(22) Filed: Oct. 6, 2004

(65) Prior Publication Data

US 2005/0144222 A1    Jun. 30, 2005

Related U.S. Application Data

(63) Continuation-in-part of application No. 09/846,037, filed on Apr. 29, 2001.

(51) Int. Cl.
G06K 9/00 (2006.01)
G06F 15/16 (2006.01)

(52) U.S. Cl. ............... 382/128; 382/100; 709/203

(58) Field of Classification Search ........... 382/154, 382/243, 265, 100, 128; 345/419; 709/203, 709/249; 433/3, 24, 223; 705/3, 7
See application file for complete search history.

(56) References Cited

U.S. PATENT DOCUMENTS

| | | | |
|---|---|---|---|
| 5,911,044 A | 6/1999 | Lo et al. ............... 709/203 |
| 6,072,496 A | 6/2000 | Guenter et al. ........ 345/419 |
| 6,217,334 B1 | 4/2001 | Hultgren .............. 433/215 |
| 6,261,248 B1 | 7/2001 | Takaishi et al. ......... 600/590 |
| 6,315,553 B1 * | 11/2001 | Sachdeva et al. ......... 433/24 |
| 6,438,266 B1 | 8/2002 | Bajaj et al. ............. 382/243 |
| 6,464,496 B1 * | 10/2002 | Sachdeva et al. ........ 433/24 |
| 6,466,700 B1 | 10/2002 | Makram-Ebeid ......... 382/265 |
| 6,549,819 B1 | 4/2003 | Danduran et al. ........ 700/98 |
| 6,575,751 B1 * | 6/2003 | Lehmann et al. ....... 433/223 |
| 6,608,628 B1 | 8/2003 | Ross et al. ............. 345/619 |
| 6,608,682 B2 * | 8/2003 | Ortyn et al. ........... 356/419 |
| 6,611,617 B1 | 8/2003 | Crampton .............. 382/154 |
| 6,775,712 B2 | 8/2004 | Sakai et al. ............ 709/249 |
| 6,786,726 B2 * | 9/2004 | Lehmann et al. ....... 433/223 |
| 6,816,159 B2 | 11/2004 | Solazzi ................. 345/419 |
| 6,874,131 B2 | 3/2005 | Blumberg .............. 715/513 |
| 2002/0069201 A1 | 6/2002 | Cheng ................... 707/10 |

OTHER PUBLICATIONS

National Science Foundation Award Abstract #9713906, "FACILE: A Clean Interface Design and Fabrication of Mechanical Parts," 2 pages (Aug. 15, 1997).

Ryou, O. et al., "FACILE: A Clean Interface for Design and Fabrication of Mechanical Parts," NSF Grant #DMI-9713906, pp. i-v, and 1-80 (Sep. 2001).

* cited by examiner

Primary Examiner—Anh Hong Do
(74) Attorney, Agent, or Firm—Merchant & Gould P.C.

(57) ABSTRACT

A method of dental restoration treatment utilizing the electronic delivery of an electronic model image of the dental restoration treatment. The method includes generating an electronic model image of a proposed dental restoration treatment; storing the electronic model image within computer readable memory of a server-based computing system; delivering the electronic model image to a doctor having a remote client computer over a distributed communications network; and displaying the electronic model image upon the remote client computer and performing analysis of the electronic model image. The doctor is provided with a variety of viewing and analysis tools, and can add notations to the electronic model image.

20 Claims, 31 Drawing Sheets

METHOD AND APPARATUS FOR INTERACTIVE REMOTE VIEWING AND COLLABORATION OF DENTAL IMAGES

CROSS REFERENCE TO RELATED APPLICATION

This is a continuation-in-part of application Ser. No. 09/846,037, filed on Apr. 29, 2001, currently pending, the entire disclosure of which is hereby incorporated by reference.

TECHNICAL FIELD

The invention relates generally to a distributed computing system for the creation and distribution of electronic models of objects and more particularly to a system, method and article of manufacture for delivering and manipulating electronic model images to end users using a distributed computing system.

BACKGROUND

Computational resources available for use by various end users of computing systems has increased significantly. This increase in capability of systems has created the ability for many more end users to utilize computer based image systems to replace processes that utilize paper and physical model processes. In the past, computer aided design, drafting, and manufacture (CAD/CAM) tools represented an area of applications in which computer based image systems have migrated from paper and model based processes to electronic systems.

These CAD/CAM systems typically consist of design and drafting tools that allow technical designers to build systems that were previously designed on paper using draftsmen. Over time, the computing system and their respective tools have allowed increasing interactive manipulation of components during the design process. This advance in design of items that are then manufactured has occurred using these computer aided systems.

These CAD/CAM systems, however, typically start their processes with a set of pre-defined libraries of components that may be used by the user of the computing system. For example, electronic schematics possess a library of components that are used to specify a circuit and its layout. The creation of these libraries, as well as the amount of computational resources needed to perform the operations related to these systems, has prevented the wide-spread use of these systems in other areas of technology.

With the advances recently made in computational systems, these computer based image systems may be used to permit end users to replace paper and physical models with electronic images. Two areas of technology present additional obstacles to the more widespread use of these systems. First, a mechanism to capture image representations of physical objects accurately and with sufficient resolution is needed in a form that is both inexpensive to operate while providing rapid turn-around for users. Second, a mechanism to easily transmit the images to end users from the location where the image representation of physical objects are generated is also needed. Neither of these latter obstacles has been overcome in existing imaging systems.

SUMMARY

The present invention relates to a method, apparatus, and article of manufacture for delivering and manipulating electronic model images to end users using a distributed computing system.

In one aspect of the invention, a method for providing electronic delivery of an electronic model image of a dental restoration treatment is provided. The method comprises generating an electronic model image of a proposed dental restoration treatment, storing the electronic model image within computer readable memory of a server-based computing system, delivering the electronic model image to a doctor having a remote client computer over a distributed communications network, and displaying the electronic model image upon the remote client computer and performing analysis of the electronic model image.

In one embodiment, notations can be added to the electronic model image to allow the doctor to comment on, and suggest changes to, the dental restoration treatment. The electronic model image with the attached notations can then be transmitted to a laboratory to make any necessary corrections to the image or to begin fabrication of the dental restoration.

In another aspect of the invention, a method of dental restoration treatment is provided. The method comprises displaying an electronic model image of a proposed dental restoration treatment upon a display device, performing an analysis of the electronic model image to determine whether or not the proposed dental restoration treatment is appropriate, and attaching a notation to the electronic model image that is displayed.

These and various other advantages and features of novelty which characterize the invention are pointed out with particularity in the claims annexed hereto and form a part hereof. However, for a better understanding of the invention, its advantages, and the objects obtained by its use, reference should be made to the drawings which form a further part hereof, and to accompanying descriptive matter, in which there are illustrated and described specific examples of an apparatus in accordance with the invention.

DETAILED DESCRIPTION

The present invention relates to a code generation method, apparatus, and article of manufacture for providing a distributed computing system for the creation and distribution of electronic models of objects.

Figure 1:
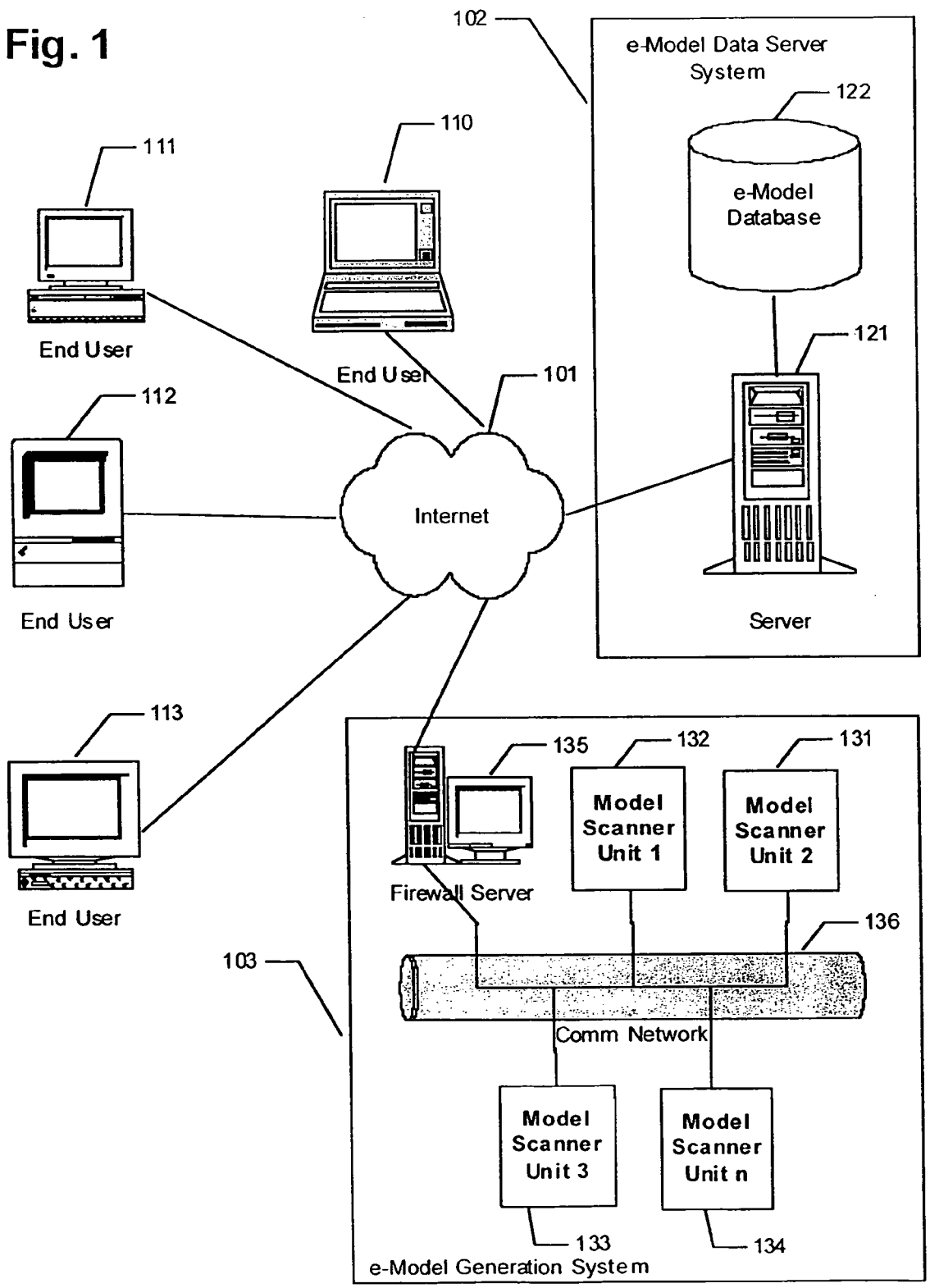
FIG. 1 illustrates a distributed computing system for the creation and distribution of electronic models of objects according to one embodiment of the present invention.

FIG. 1 illustrates a distributed computing system for the creation and distribution of electronic models of objects according to one embodiment of the present invention. End users operate a plurality of different computing systems 110–113 to perform their respective computing tasks. End users typically use one general purpose computing system for a variety of tasks. Accordingly, to insure the practicality and adoption of an imaging system designed to replace paper and model based systems, the imaging system used by end users 110–113 preferably consists of laptop and/or desktop style personal computers.

These computing systems typically possess a mechanism to communicate with other computing systems over a communications network 101. The Internet 101, as a publicly available communications network, provides an available communications path between virtually any two computing systems after they first connect to the Internet. While other communications mechanisms exist and may be used, the Internet provides a well-known mechanism to communicate data between two computing systems.

In an image-based eModel system, an end user 110 communicates over a communications network 101 to a server 121 to retrieve electronic eModels from a database 122. The end user 110 may be located anywhere a connection to the communications network 101 exists to retrieve the eModels from the database 122. This database 122 may be located within an eModel data server system 102 that is maintained by third parties that provide maintenance, data back up, and similar data processing overhead functions that are not an overriding concern for an end user. This data back-up, for example, may consist of long-term archiving of data to replace maintenance of physical models that have in the past required a great deal of effort and expense to complete.

The eModels themselves consist of a data file stored on the server 121 in a database 122 that allows quick and efficient access for users. These eModels are generated in a separate eModel generation system 103 that consists of one or more model scanning units 131–134. These units 131–134 are connected together using a local communications network 136 and a communications path 135 to the Internet 101. As such, eModels, once generated may be transferred to the eModel Data server system 102 for ultimate use by end users 110–113.

Figure 2:
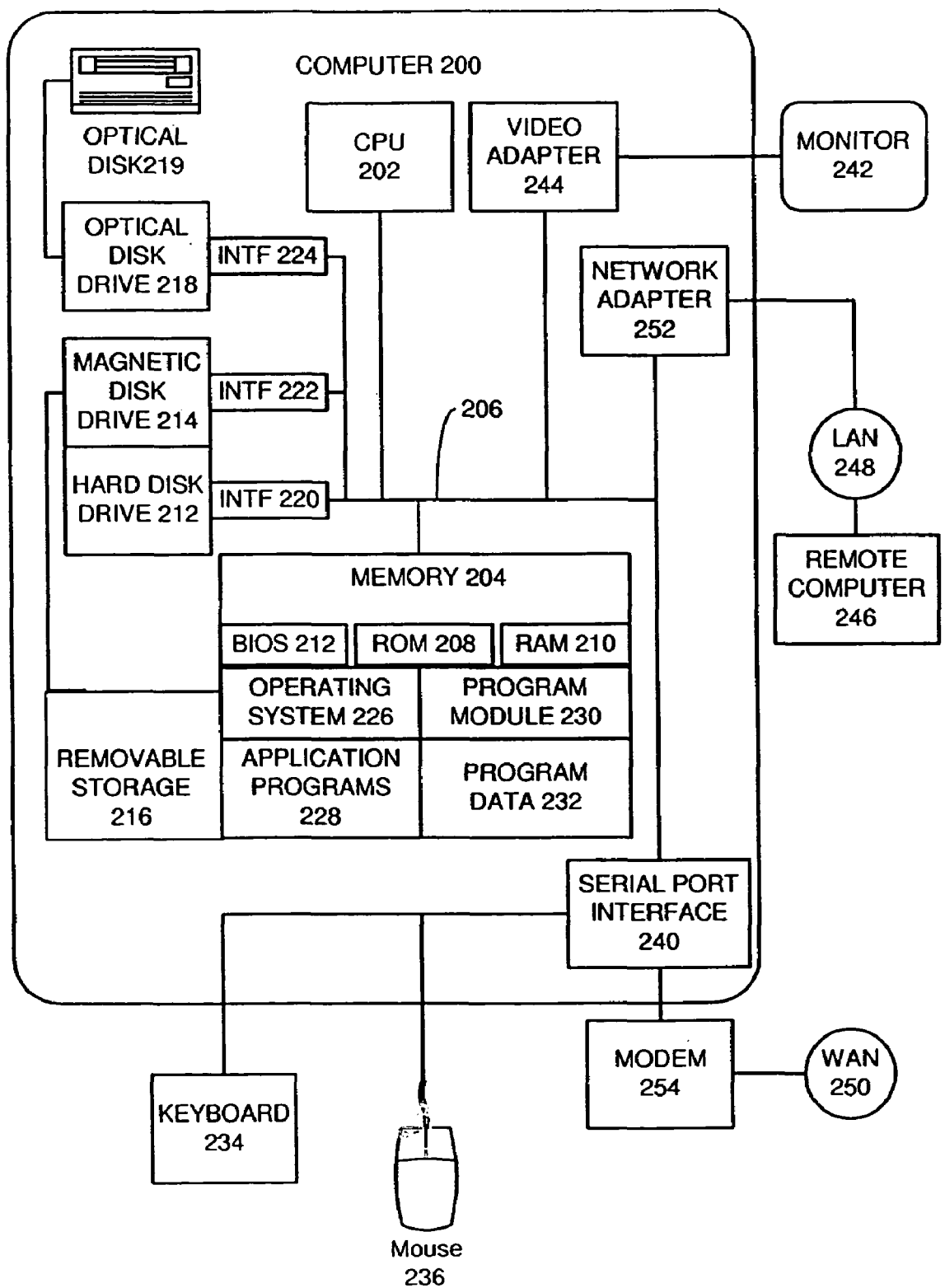
FIG. 2 illustrates an exemplary computing system useful for implementing an embodiment of the present invention.

With reference to FIG. 2, an exemplary system for implementing the invention includes a general-purpose computing device in the form of a conventional personal computer 200, including a processor unit 202, a system memory 204, and a system bus 206 that couples various system components including the system memory 204 to the processor unit 202. The system bus 206 may be any of several types of bus structures including a memory bus or memory controller, a peripheral bus and a local bus using any of a variety of bus architectures. The system memory includes read only memory (ROM) 208 and random access memory (RAM) 210. A basic input/output system 212 (BIOS), which contains basic routines that help transfer information between elements within the personal computer 200, is stored in ROM 208.

The personal computer 200 further includes a hard disk drive 212 for reading from and writing to a hard disk, a magnetic disk drive 214 for reading from or writing to a removable magnetic disk 216, and an optical disk drive 218 for reading from or writing to a removable optical disk 219 such as a CD ROM, DVD, or other optical media. The hard disk drive 212, magnetic disk drive 214, and optical disk drive 218 are connected to the system bus 206 by a hard disk drive interface 220, a magnetic disk drive interface 222, and an optical drive interface 224, respectively. The drives and their associated computer-readable media provide nonvolatile storage of computer readable instructions, data structures, programs, and other data for the personal computer 200.

Although the exemplary environment described herein employs a hard disk, a removable magnetic disk 216, and a removable optical disk 219, other types of computer-readable media capable of storing data can be used in the exemplary system. Examples of these other types of computer-readable mediums that can be used in the exemplary operating environment include magnetic cassettes, flash memory cards, digital video disks, Bernoulli cartridges, random access memories (RAMs), and read only memories (ROMs).

A number of program modules may be stored on the hard disk, magnetic disk 216, optical disk 219, ROM 208 or RAM 210, including an operating system 226, one or more application programs 228, other program modules 230, and program data 232. A user may enter commands and information into the personal computer 200 through input devices such as a keyboard 234 and mouse 236 or other pointing device. Examples of other input devices may include a microphone, joystick, game pad, satellite dish, and scanner. These and other input devices are often connected to the processing unit 202 through a serial port interface 240 that is coupled to the system bus 206. Nevertheless, these input devices also may be connected by other interfaces, such as a parallel port, game port, or a universal serial bus (USB). A monitor 242 or other type of display device is also connected to the system bus 206 via an interface, such as a video adapter 244. In addition to the monitor 242, personal computers typically include other peripheral output devices (not shown), such as speakers and printers.

The personal computer 200 may operate in a networked environment using logical connections to one or more remote computers, such as a remote computer 246. The remote computer 246 may be another personal computer, a server, a router, a network PC, a peer device or other common network node, and typically includes many or all of the elements described above relative to the personal computer 200. The network connections include a local area network (LAN) 248 and a wide area network (WAN) 250. Such networking environments are commonplace in offices, enterprise-wide computer networks, intranets, and the Internet.

When used in a LAN networking environment, the personal computer 200 is connected to the local network 248 through a network interface or adapter 252. When used in a WAN networking environment, the personal computer 200 typically includes a modem 254 or other means for establishing communications over the wide area network 250, such as the Internet. The modem 254, which may be internal or external, is connected to the system bus 206 via the serial port interface 240. In a networked environment, program modules depicted relative to the personal computer 200, or portions thereof, may be stored in the remote memory storage device. It will be appreciated that the network connections shown are exemplary, and other means of establishing a communications link between the computers may be used.

Additionally, the embodiments described herein are implemented as logical operations performed by a computer. The logical operations of these various embodiments of the present invention are implemented (1) as a sequence of computer implemented steps or program modules running on a computing system and/or (2) as interconnected machine modules or hardware logic within the computing system. The implementation is a matter of choice dependent on the performance requirements of the computing system implementing the invention. Accordingly, the logical operations making up the embodiments of the invention described herein can be variously referred to as operations, steps, or modules.

Figure 3:
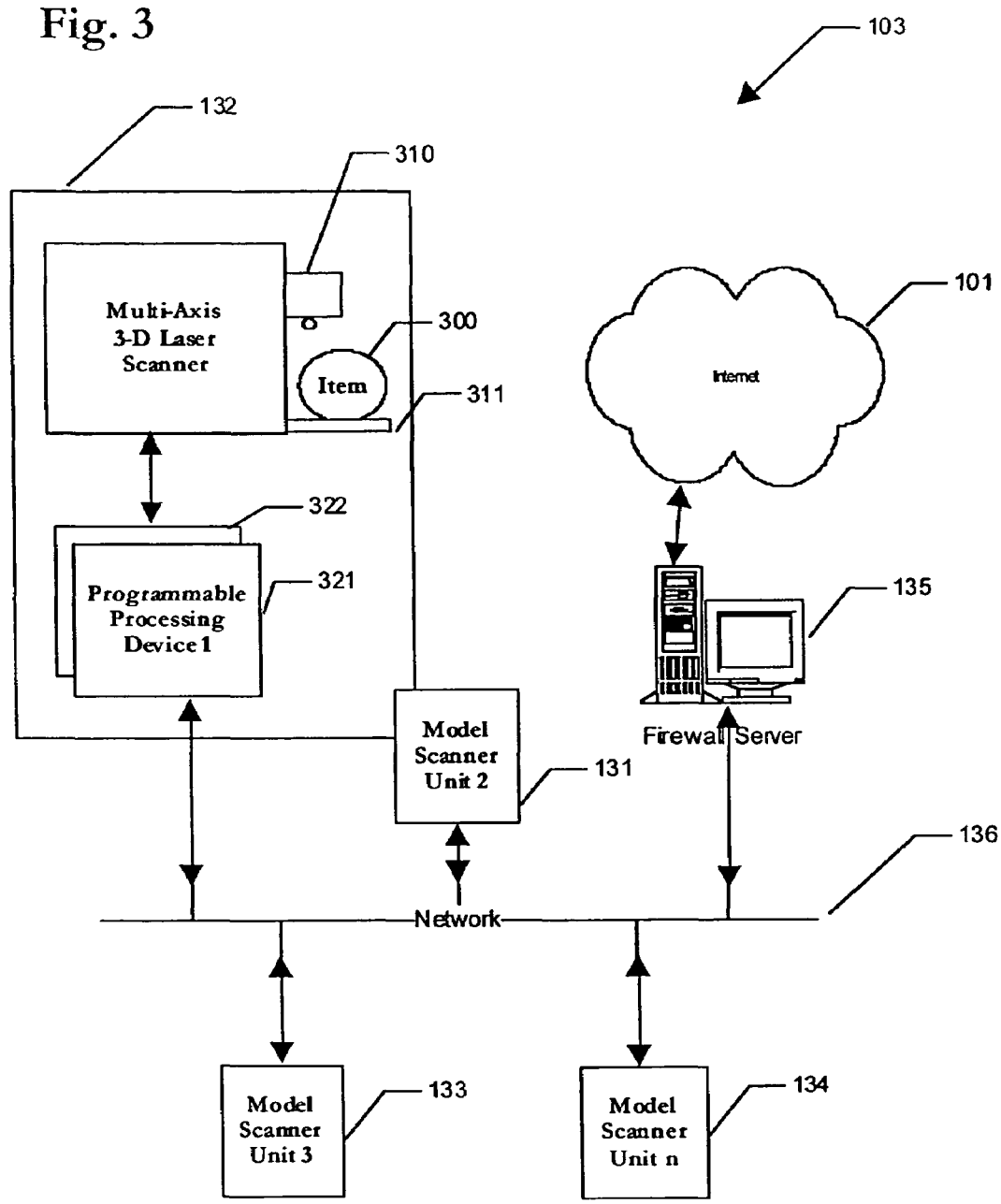
FIG. 3 illustrates an eModel generation system according to an embodiment of the present invention.

FIG. 3 illustrates an eModel generation system according to an embodiment of the present invention. The eModel generation system 103 is an object scanning facility having one or more model scanner units 131–134 that scan user objects 300 using a laser scanner 310 that mounts the user object 300 on a multi-axis scanning platform 311. The laser scanner 310 interfaces with one or more programmable processing devices 321–322 to process the laser scanner data into usable object image data. These model scanner units 131–134 are connected together using a data communications network 136 to permit the image data to be transferred between processing devices. Ultimately, the eModel data is transferred to a data server 102 over a communications network 101 like the Internet.

In one embodiment, each model scanner unit 132 includes two processing devices 321–322 to process the laser scanner data and generate the model image data. In this embodiment, the processing utilizes one such computing device 321 to processing the scanner data to generate a polygonal mesh of triangles and utilizes a second computing system 322 to further process the initial polygonal mesh into a reduced set of surfaces that may be ultimately used by an end user. One skilled in the art will recognize that these two computing devices may in fact be constructed using any number of programmable computing devices where the computing capacity of the devices used will determine the amount of time needed to complete a given processing task. As such, other embodiments of the present invention may be used for these computing devices without deviating from the spirit and scope of the present invention as recited within the attached claims.

In a preferred embodiment, the laser scanner 310 is a line scanner of the type made by Laser Design, Incorporated of Bloomington Minn., Model No. RPS-120. The scanner possesses a capability to transfer data to a computing system 321 at a rate of 14,400 data points per second and have a resolution of 12 microns. In order to create adequate eModels for user items, the scanner 310 possesses a volumetric accuracy of approximately 25 microns. The multi-axis platform 311 rotates the user item 300 within the field of view of the laser scanner 310 in order to collect sufficient data points from all orientations to observe the entire surface of the user object 300.

Figure 4:
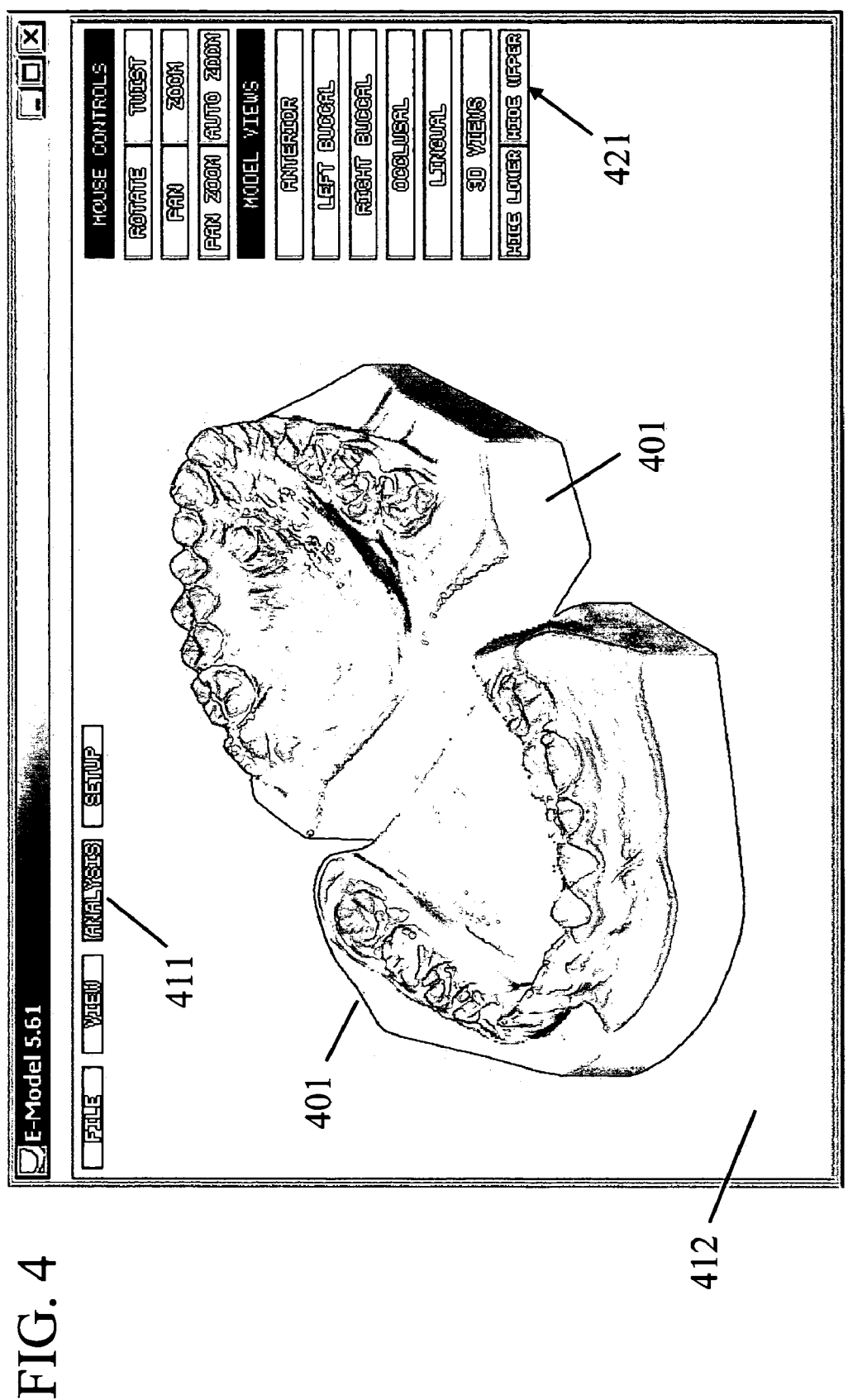
FIG. 4 illustrates an eModel for an impression of a patient's mouth and teeth according to yet another example embodiment of the present invention.

FIG. 4 illustrates an eModel for an impression of a patient's mouth and teeth according to yet another example embodiment of the present invention. In this example, an impression of a patient's mouth and teeth are obtained from a dental care provider. From the impression, a plaster model of the upper and lower teeth are obtained. These models have been typically used by dental care providers to observe and measure a patient's mouth and teeth when planning how a course of dental care treatment is to progress. According to the present invention, the plaster model is scanned in the eModel generation system 103 to generate the upper 402 and lower 401 eModels that correspond to a digital image representation of the plaster model.

Once the digital eModel is obtained, the plaster model is no longer needed. As such, the storage of the model is no longer required by dental care providers, as has been the case for most of the past practices of dental care providers. Because the eModel is a digital representation of the physical model, a plurality of user controls 411–412 are used by the end user to view the user item 300, in this case the patient's teeth 401–402, from any orientation. Measurements and other manipulations of the eModel are also permitted.

Figure 5:
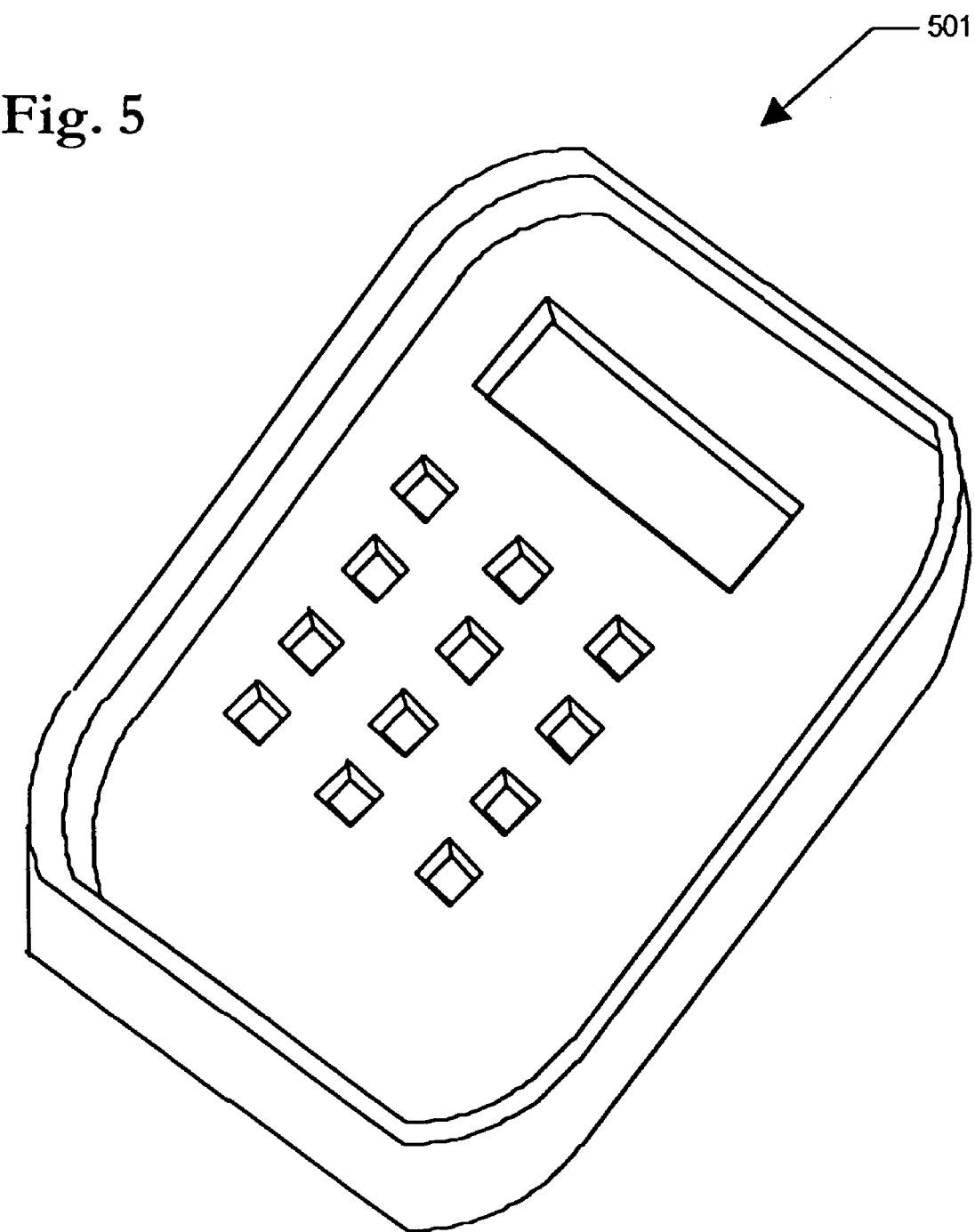
FIG. 5 illustrates an eModel for a shell from a cellular telephone case according to yet another example embodiment of the present invention.

FIG. 5 illustrates an eModel for a shell from a cellular telephone case according to yet another example embodiment of the present invention. In this second example, a shell from a cellular telephone 501 corresponds to the user item 300 that is scanned to generate an eModel. Any user item 300 that is small enough to fit within the scanning space of the scanner 310 and multi-axis platform 311 in the eModel generation system 103 may be used to generate an eModel. In the preferred embodiment, the user item is less than a 6-inch volumetric cube. One skilled in the art will recognize that other scanning devices that produce scanned image data at a sufficiently small resolution that permits larger items to be scanned may also be used without deviating from the spirit and scope of the present invention as recited within the attached claims. In addition, the nature and shape of the user item 300, whether it corresponds to a model of a patient's mouth and teeth or corresponds to a component of an item of manufacture, does not change the operation of the present invention as recited within the attached claims.

Figure 6:
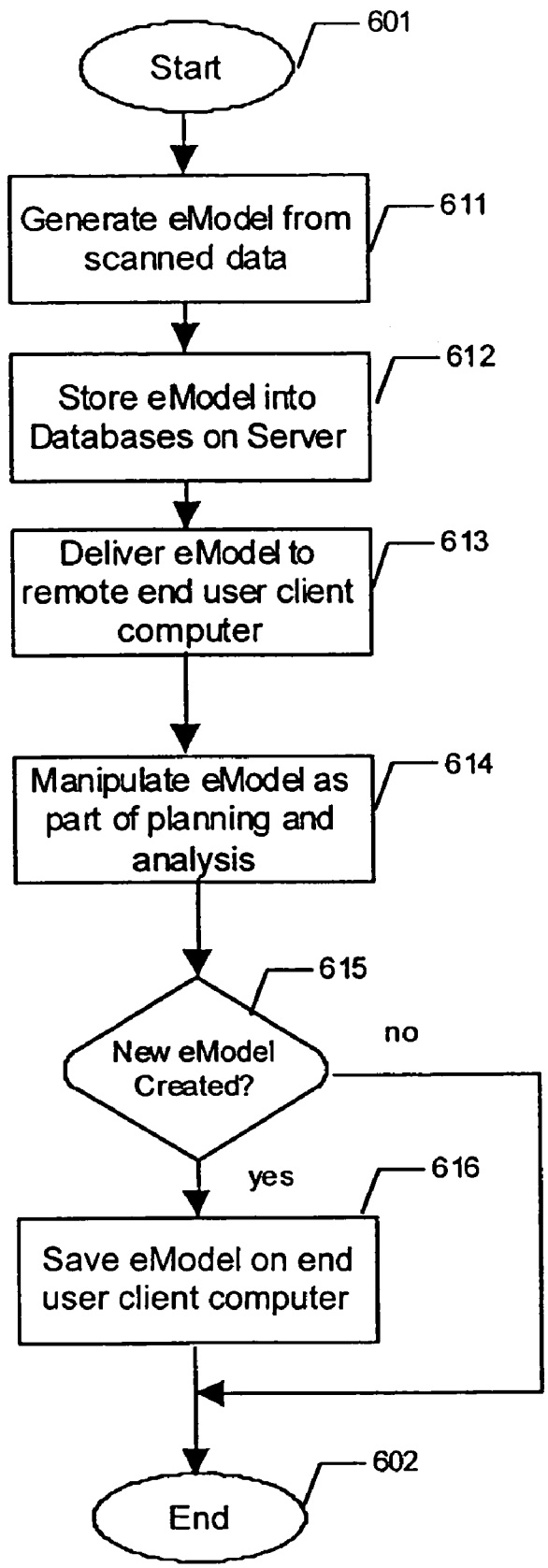
FIG. 6 illustrates a block diagram for an eModel generation and distribution system according to an embodiment of the present invention.

FIG. 6 illustrates a block diagram for an eModel generation and distribution system according to an embodiment of the present invention. The process starts 601 and an eModel is generated from a scan of an end user item in module 611. Once the eModel is generated, the model is stored within a data storage medium on a remotely accessible server in module 612. Next, an end user receives an eModel of interest for use on his or her client computer over a communications network in module 613.

Once an end user receives the eModel, the end user may view and manipulate the eModel as needed to complete any planning, analysis and similar operations in module 614. Test module 615 determines if a new eModel has been created as part of the end user's manipulation of an eModel and if the newly created eModel should be saved for later use. If the new eModel exists and is to be saved, module 616 saves the eModel locally on the end user client computer for later use and the processing ends 602. If test module 615 determines that a new eModel is not to be saved, the processing also ends 602.

Figure 7:
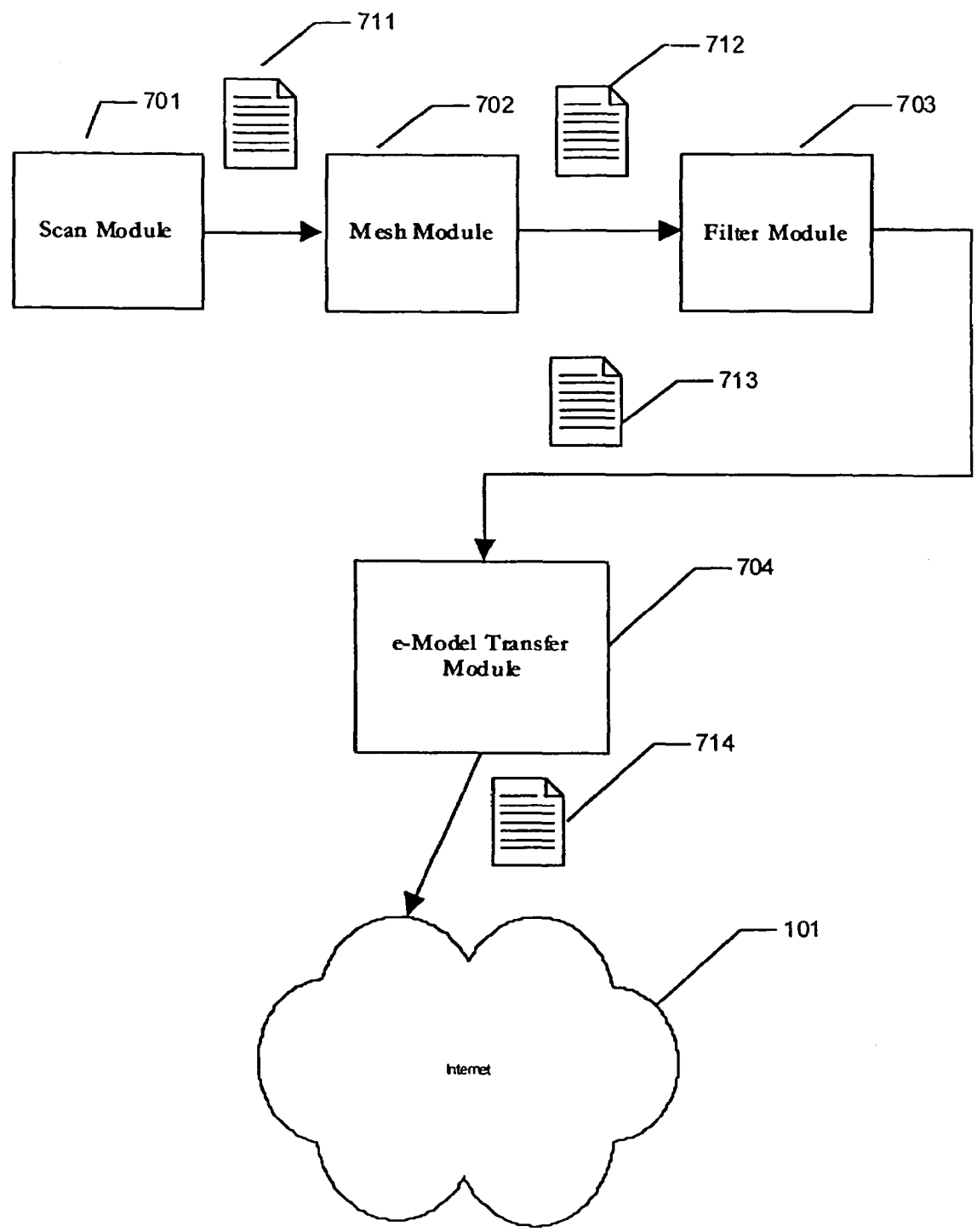
FIG. 7 illustrates a block diagram for an eModel generation process according to yet another example embodiment of the present invention.

FIG. 7 illustrates a block diagram for an eModel generation process according to yet another example embodiment of the present invention. The process for generating an eModel of a user item 300 starts when a scan module 701 utilizes a scanner 310 to generate a point cloud data file 711. For objects that typically fit within the 6 inch volumetric cube of the scanner, this point cloud data file 711 may comprises between 2 and 3 million data points. The large amount of data points generated from the scan of a single user item 300 has posed a significant limitation upon the use of eModels in the past. In the preferred embodiment, the scanning process implemented in the scan module 701 is performed within the first of two programmable processors 321 within a given model scanner unit 132.

The point cloud data file 711 represents a data point for each location on the surface of the user item 300. The file is processed into a polygonal mesh of triangles in a mesh module 702. In this process, the points from the point cloud data file are organized into triangles of neighboring points that describe the surface of the user item 300 that has been scanned. The creation of a polygonal mesh data file 712 that contains the specification of all of the triangles reduces the amount of data to between 100–300 k triangles.

The number of triangles that are used to describe a surface of the user item 300 may be reduced further in a filtering module 703 when a reduced polygonal mesh file 713 is created. This reduction of the number of triangles is accomplished when adjacent triangles are sufficiently co-planer to permit the surface described by two or more triangles to be similarly described using a single triangle. The reduced polygonal mesh data file 713 typically consists of 60 k triangles that permits a manageable amount of data to be used when eModels are processed.

The eModel are completed by an eModel transfer module 704 that attaches a file header that describes the user item in sufficient detail that it maybe retrieved at a later date. The eModel is contained within an eModel data file 714 that may be transmitted over the Internet 101 to the eModel data server for storage within its database.

Figure 8A:
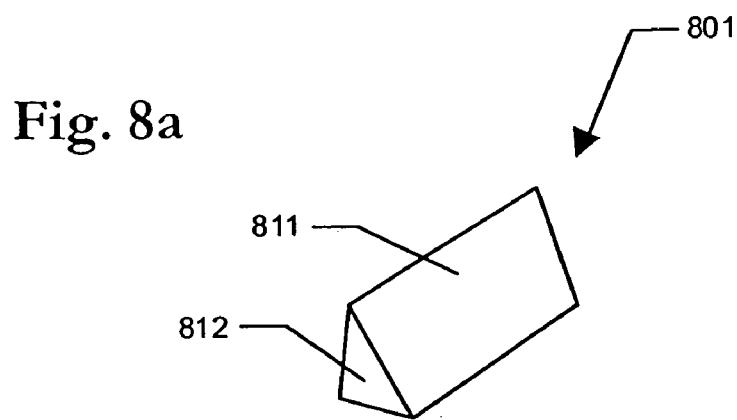
FIGS. 8a–b illustrate an example of an object from which an eModel is generated according to yet another example embodiment of the present invention.
Figure 8B:
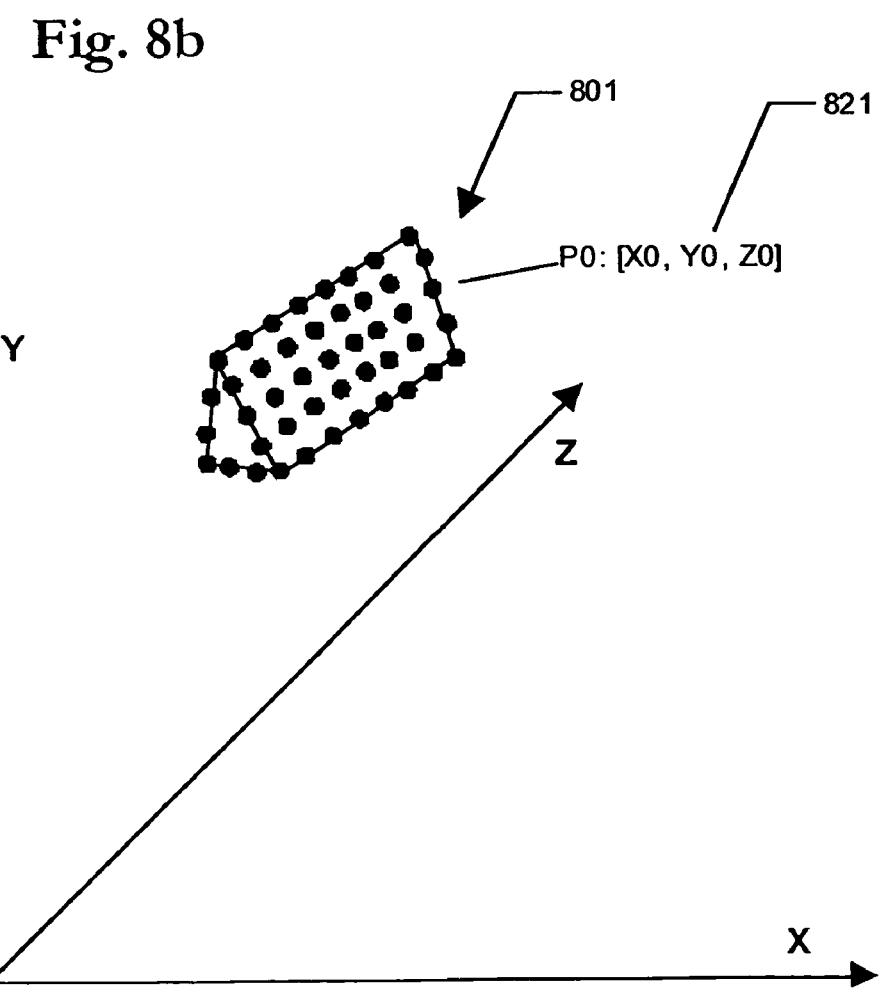

FIG. 8a–b illustrate an example of an object from which a eModel is generated according to yet another example embodiment of the present invention. A simple geometric 3D shape 801 is presented as an example of how a reduced polygonal mesh is generated that may be used as an eModel. This shape 801 has two visible faces: a small triangular side face 812 and a larger rectangular face 811. Three other faces make up this simple object that are not visible from the perspective shown in FIG. 8a.

FIG. 8b shows this object 801 having a set of surface data points superimposed upon the object 801 faces. When a laser line scanner passes its sensor over a face of the object 801, a line of points corresponding to the position of the objects' surface are obtained. These points are separated by the spatial resolution of the scanner. The data points, P0 821 are specified using a 3 coordinate position X0, Y0, Z0. As the object 801 is moved within the scanning area of the multi-axis platform, the scanner translates the data points to a common coordinate system such that the collection of all points represents the points in a 3D coordinate system that corresponds to the surface of the item 801. These data points are contained within the point cloud data file 711 that is generated by the scan module 701.

Figure 9:
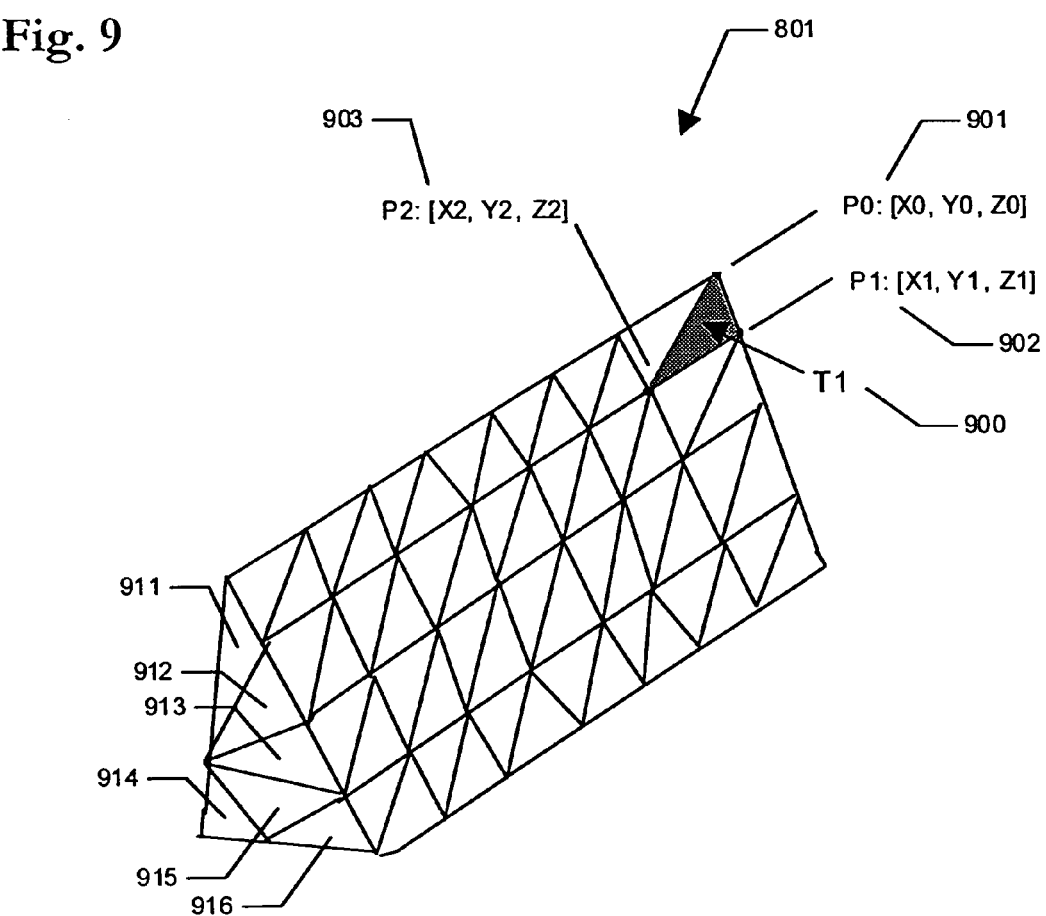
FIG. 9 illustrates a representation of the object in FIG. 8 using a polygonal mesh according to an embodiment of the present invention.

FIG. 9 illustrates a representation of the object in FIG. 8 using a polygonal mesh according to an embodiment of the present invention. As discussed above, the point cloud data file 711 is reduced to a polygonal mesh of triangles in which the surface of the triangles are used to approximate the surface of the item 801. In this example, a triangle, T1 900, is located on the larger surface 811 of the item 801. The triangle T1 900 is specified using the three corner points P0 901, P1 902, and P2 903. As before, each of these three points are specified using a 3D coordinate system such that T1 900 is defined:

T1: {P0, P1, P2} or

T1: {[X0, Y0, Z0], [X1, Y1, Z1], {[X2, Y2, Z2]}.

Each triangle in the polygonal mesh is specified using the three points as shown above. No particular order for the points making up the triangle is necessary. The smaller side 812 of the item 811 in this example is initially shown with six triangles 911–916. The triangles in the polygonal mesh may be created using any number of well known methods for reducing point position data into a polygonal mesh that approximates the surface of the object.

Figure 10:
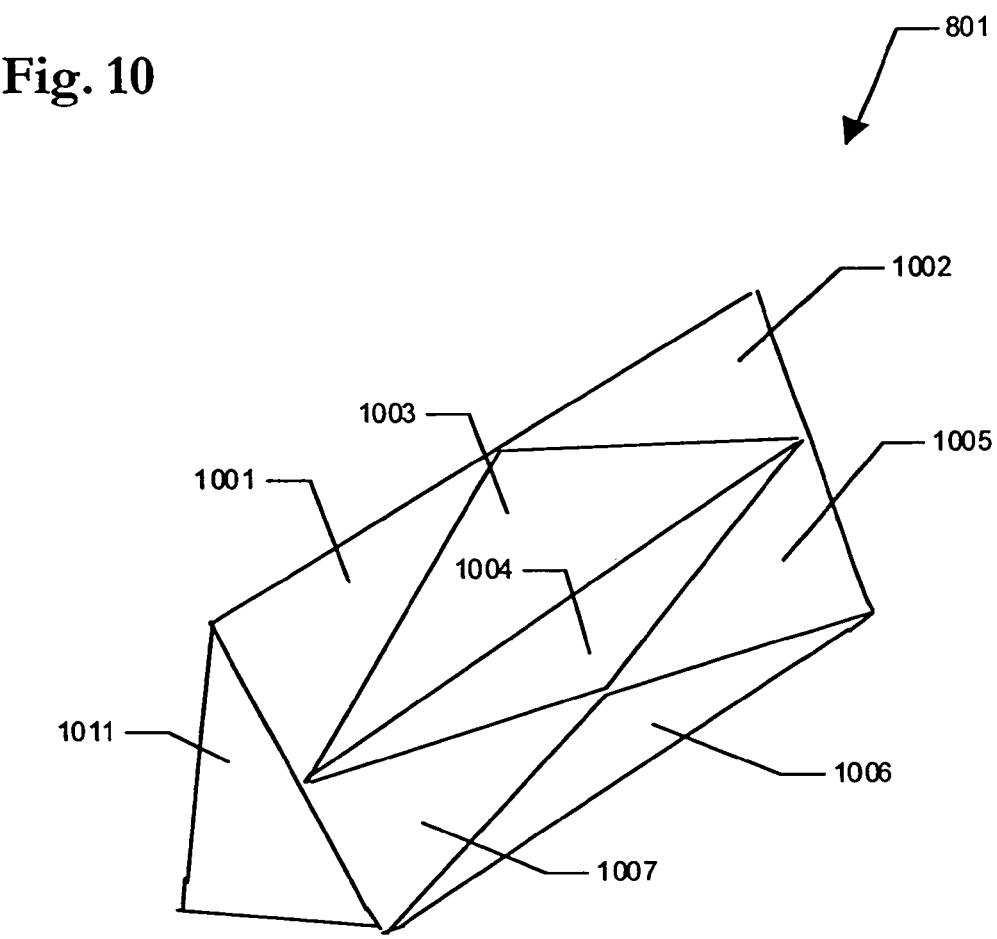
FIG. 10 illustrates a simplified representation of the object in FIG. 8 using a reduced polygonal mesh according to yet another example embodiment of the present invention.

FIG. 10 illustrates a simplified representation of the object in FIG. 8 using a reduced polygonal mesh according to yet another example embodiment of the present invention. A reduced polygonal mesh is generated by combining adjacent triangles in the original polygonal mesh when the two or more triangles are sufficiently coplanar that they may be represented using a single triangle. In this example, a large number of small triangles may have been originally generated on the mesh shown in FIG. 9. When a flat surface of the simple object 801 is considered, the number of triangles needed is reduced significantly 1001–1007. In the example, all of the small triangles from the small side 812 of the item 801 have been combined into a single triangle 1011. The processing associated with this filtering operation controls the amount of triangle combinations by setting a threshold relating to the minimum amount of deviation from a single plane for the two or more triangles that is permitted before two or more triangles are required to remain separate. This filtering process may be accomplished using a number of commercially available polygonal mesh processing products without deviating from the present invention as recited within the attached claims.

Figure 11:
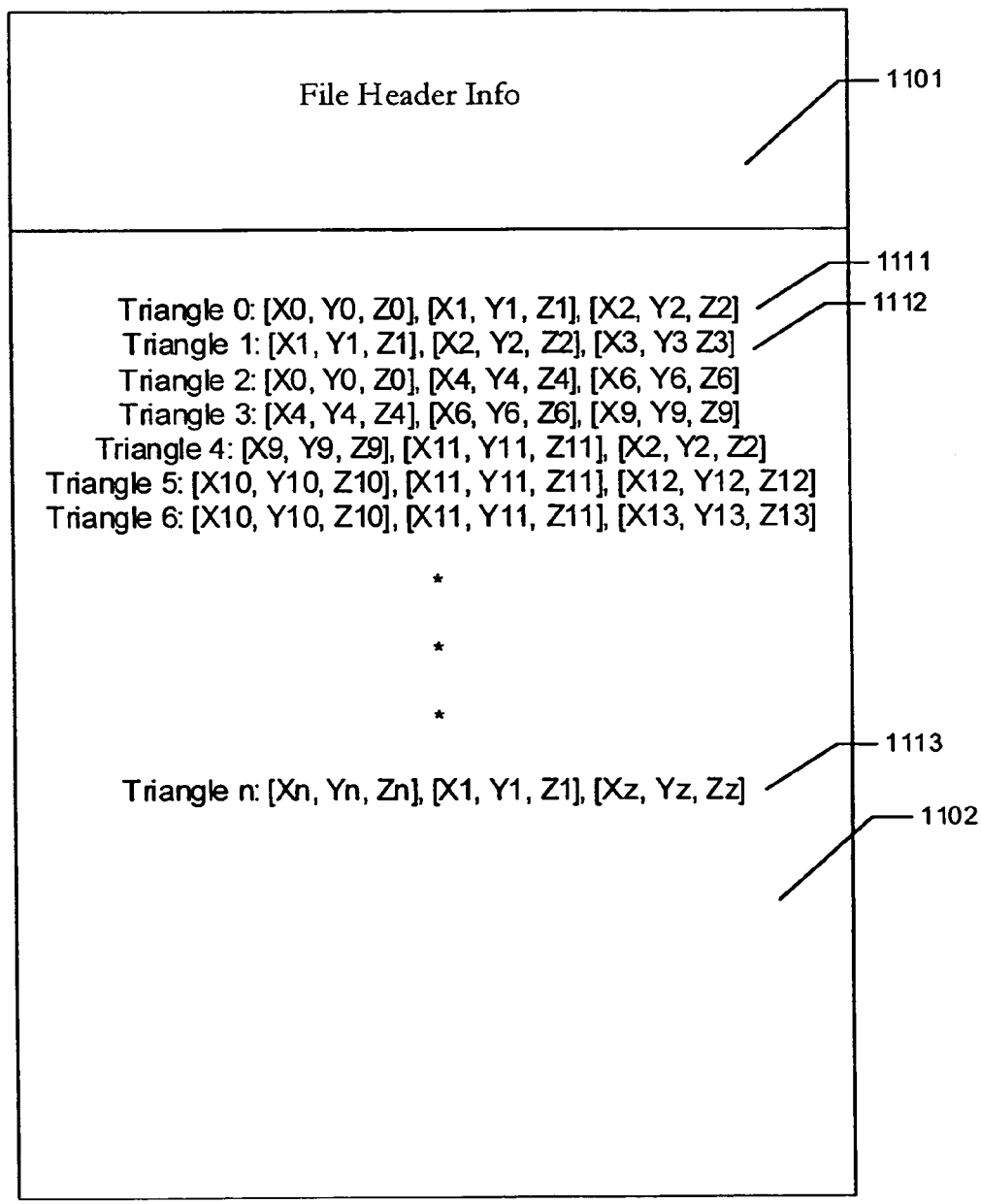
FIG. 11 illustrates a format for an eModel data file according to yet another example embodiment of the present invention.

FIG. 11 illustrates a format for an eModel data file according to yet another example embodiment of the present invention. The eModel data file consists of a file header info block 1101 and a triangle specification block 1102. The triangle specification block consists of the set of triangle definitions 1111–1113 that are used to define the reduced polygonal mesh. The file header info block 1101 includes a set of searchable identification information that may be used to identify a particular model from any number of related models. The mouth and teeth eModels, for example, will likely contain patient identification information such as name, date of birth, address, social security number that may be used to uniquely identify the patient from which the model was generated. The info block 1101 may also contain dental care provider information such as the dentist name and address as well as the date on which the impression was taken that generated the eModel.

For other items, such as the cellular phone shown in FIG. 5, any useful identifying information may be used. This data is typically ASCII encoded data that may be easily searched and processed as necessary. One skilled in the art will recognize how this file header info block 1101 may be modified to include any information needed by a particular application without deviating from the spirit and scope of the present invention as recited within the attached claims.

Figure 12:
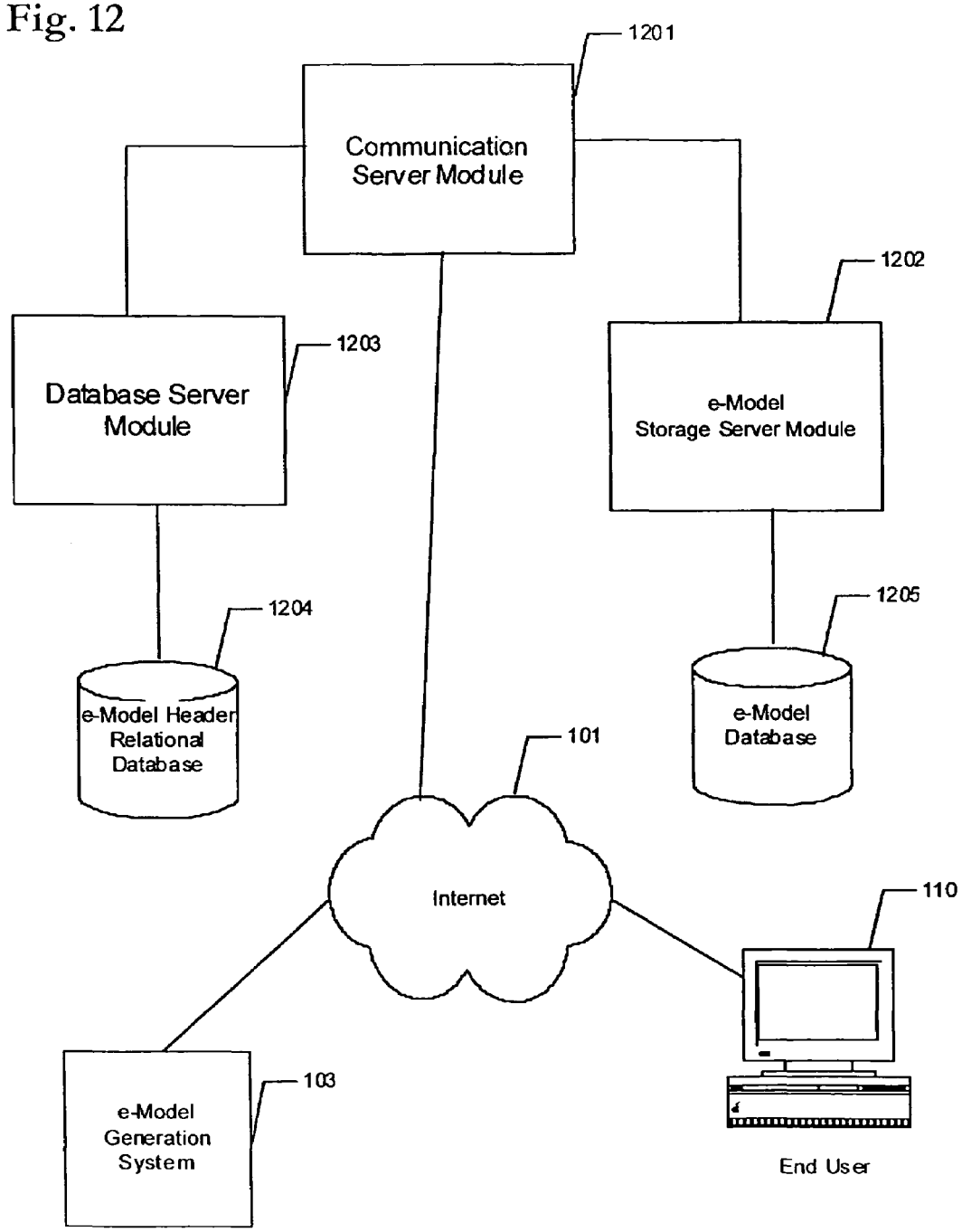
FIG. 12 illustrates an eModel data server system according to yet another an embodiment of the present invention.

FIG. 12 illustrates an eModel data server system according to an embodiment of the present invention. The eModel data server 102 communicates with the eModel generation system 103 and end users 110 over a communications network 101. The eModels that are generated are transmitted to the eModel data server 102 for storage in its databases 1204–1205 for later user.

The eModel data server 102 includes a communications server module 1201, a database server module 1203, and an eModel storage server module 1202 to perform its tasks. The communications server module 1201 performs the communications functions needed to receive eModels from the generation system 103 as well as the communication functions needed to interact with end users when they wish to locate and download eModels of interest.

The eModels received from the generation system 103 are stored within two databases. A copy of the file header info block 1101 is stored within a first database 1204 and the entire eModel file is stored within a file storage database 1205. This separation allows the file header info block data to be stored within a relational database to permit rapid searching for eModels of interest. Once the identity of a desired eModel is located in the relational database 1204, the end user may request a copy of the larger eModel file from the file storage database 1205. This separation of the two database functions allows the data storage and data processing requirements of each operation to be scaled independently of each other as the nature of the end user interaction with the server is determined. If significant amounts of database query operations are occurring in a particular use of the server, the processing capabilities of the relational database may be increased. If the server is predominantly used to transfer large eModel files to users, data transfer capacity of the file storage database may be increased.

Figure 13:
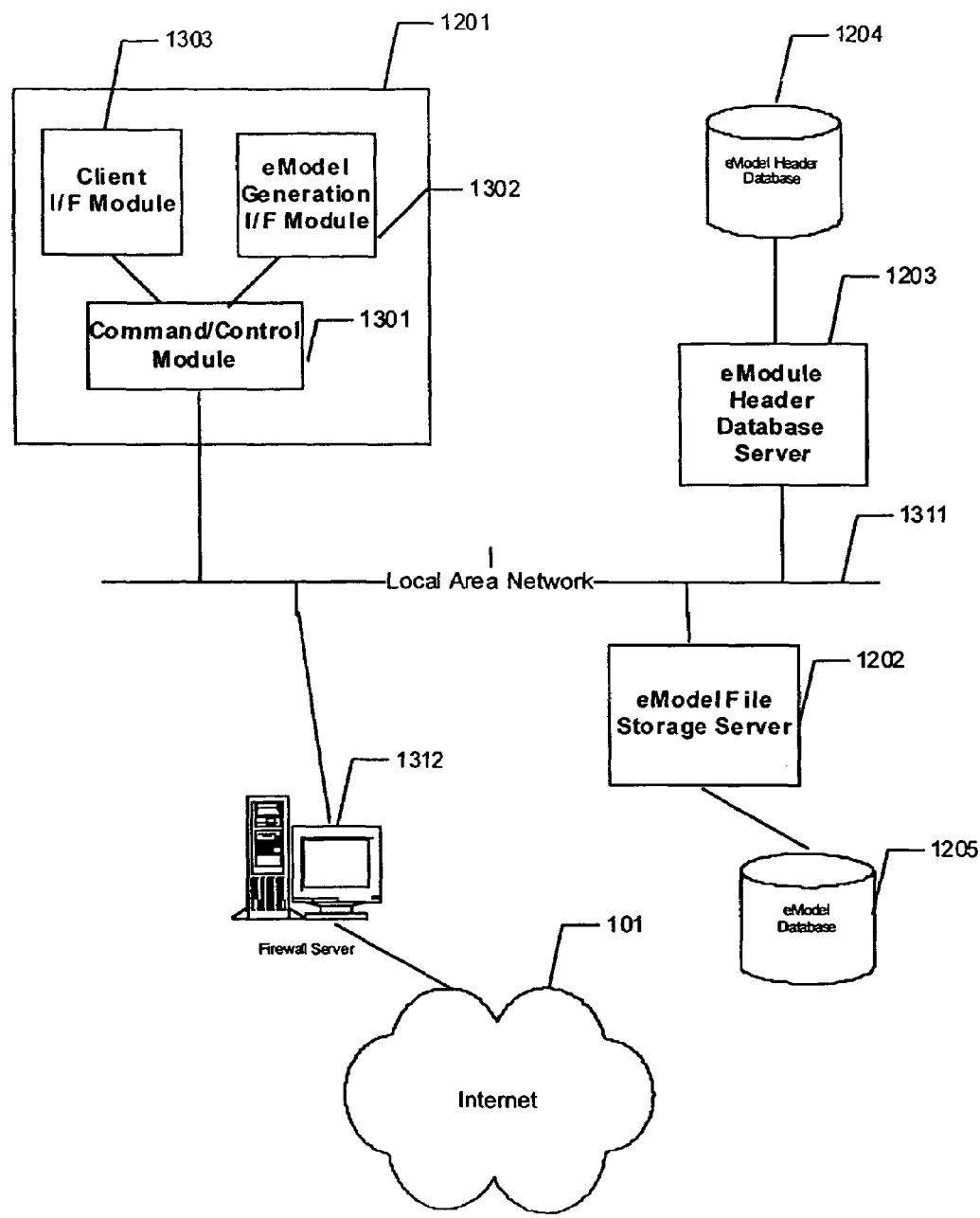
FIG. 13 illustrates another eModel data server system according to yet another example embodiment of the present invention.

FIG. 13 illustrates another eModel data server system according to yet another example embodiment of the present invention. In this particular embodiment, the communication server 1201, the eModel header database server 1203, and the eModel file storage server 1202 are all connected to a common local area network to perform the data communication operations. A firewall server 1312 connects the local area network to the Internet 101 for communications to end users 110 and the eModel generation system 103.

The eModel file header info block database 1204 is connected to the eModel header database server 1203 to provide the relational database functions needed to locate eModels of interest. The eModel database 1205 is connected to the eModel file storage server 1202 to provide the file storage for all of the eModels.

Within the communications server 1201, a command and control module 1301 receives requests for operations and coordinates the processing of the other modules and servers to complete a processing and data retrieval request. A client interface module 1303 processes the entire communication request received from an end user 110. The eModel generation interface module 1302 processes all of the communication requests from the eModel generation system 103 to accept and store new eModels within the databases 1204–1205.

In order to perform its processing functions, the communications server 1201 receives the command messages listed in Table 1. These commands allow eModels to be stored into the databases 1204–1205 and allow end users 110 to search for and retrieve eModels from the databases.

TABLE 1

Server Communication Commands

| Procedure | Parameters | Return | Description |
| --- | --- | --- | --- |
| user_get_emodel_list | USER_LOGIN_NAME, USER_PASSWORD, BEGIN_DATE, END_DATE | E_MODEL_ID, PATIENT_LAST_NAME, PATIENT_FIRST_NAME, CREATION_DATE | get emodel META data between BEGIN_DATE and END_DATE |
| lab_get_user_list | USER_LAST_NAME, USER_FIRST_NAME, USER_ADDRESS_CITY, USER_ADDRESS_STATE, USER_ORGANIZATION_NAME | USER_LOGIN_NAME, USER_TITLE, USER_LAST_NAME, USER_FIRST_NAME, USER_MIDDLE_NAME, USER_ADDRESS_CITY, USER_ADDRESS_STATE, USER_ORGANIZATION_NAME | get a list of all data for specified user |

TABLE 1-continued

Server Communication Commands

| Procedure | Parameters | Return | Description |
| --- | --- | --- | --- |
| add_lab | LAB_ORGANIZATION_NAME, LAB_LAST_NAME, LAB_FIRST_NAME, LAB_MIDDLE_NAME, LAB_TITLE, LAB_PHONE, LAB_FAX, LAB_E_MAIL, LAB_ADDRESS_STREET_1, LAB_ADDRESS_STREET_2, LAB_ADDRESS_STREET_3, LAB_ADDRESS_CITY, LAB_ADDRESS_STATE, LAB_ADDRESS_COUNTRY, LAB_ADDRESS_ZIP, LAB_LOGIN_NAME, LAB_PASSWORD | none | create a lab entry in the SQL database |
| add_iris_user | USER_ORGANIZATION_NAME, USER_LAST_NAME, USER_FIRST_NAME, USER_MIDDLE_NAME, USER_TITLE, USER_PHONE, USER_FAX, USER_E_MAIL, USER_BULK_MAIL, USER_ADDRESS_STREET_1, USER_ADDRESS_STREET_2, USER_ADDRESS_STREET_3, USER_ADDRESS_CITY, USER_ADDRESS_STATE, USER_ADDRESS_COUNTRY, USER_ADDRESS_ZIP, USER_LOGIN_NAME, USER_PASSWORD | none | create a user account in the SQL database |
| add_scanner | LAB_ID, ELECTRICAL_DRAWING, ELECTRICAL_BOM, MECHANICAL_DRAWING, MECHANICAL_BOM | none | create a scanner entry in the SQL database |
| add_scanner_serv_rec | SCANNER_ID, LAB_ID, SCANNER_CALIBRATED, SCANNER_MAINTENANCE, SCANNER_REPAIRED, SCANNER_GAGE_SN, SCANNER_GAGE_NIST, SCANNER_LASER_SN, SERVICE_START_DATE, SERVICE_FINISH_DATE, SERVICE_DESCRIPTION, SERVICE_TECHNICIAN | none | create a scanner service record entry in the SQL database |
| add_emodel | E_MODEL_ID, USER_LOGIN_NAME, SCANNER_ID, USER_DESCRIPTION, LAB_DESCRIPTION, PATIENT_LAST_NAME, PATIENT_FIRST_NAME, PATIENT_MIDDLE_NAME, PATIENT_TITLE, PATIENT_BIRTHDATE, PATIENT_ID, PATIENT_SEX, PATIENT_RACE, OPTION_FIELD, FILESERV_NAME, CREATION_DATE | none | create an emodel record in the SQL database |
| get_all_user_info | USER_LOGIN_NAME, USER_PASSWORD | USER_ORGANIZATION_NAME, USER_LAST_NAME, USER_FIRST_NAME, USER_MIDDLE_NAME, USER_TITLE, USER_PHONE, USER_E_MAIL, USER_BULK_MAIL, USER_ADDRESS_STREET_1, USER_ADDRESS_STREET_3, USER_ADDRESS_CITY, USER_ADDRESS_STATE, USER_ADDRESS_COUNTRY, USER_ADDRESS_ZIP | retrieve a listing of all information for specified user |

TABLE 1-continued

Server Communication Commands

| Procedure | Parameters | Return | Description |
| --- | --- | --- | --- |
| get_all_lab_info | LAB_LOGIN_NAME, LAB_PASSWORD | LAB_ORGANIZATION_NAME, LAB_LAST_NAME, LAB_FIRST_NAME, LAB_MIDDLE_NAME, LAB_TITLE, LAB_PHONE, LAB_E_MAIL, LAB_BULK_MAIL, LAB_ADDRESS_STREET_1, LAB_ADDRESS_STREET_3, LAB_ADDRESS_CITY, LAB_ADDRESS_STATE, LAB_ADDRESS_COUNTRY, LAB_ADDRESS_ZIP | retrieve a listing of all information for specified lab |
| update_user_info | USER_ID, USER_ORGANIZATION_NAME, USER_LAST_NAME, USER_FIRST_NAME, USER_MIDDLE_NAME, USER_TITLE, USER_PHONE, USER_FAX, USER_E_MAIL, USER_BULK_MAIL, USER_ADDRESS_STREET_1, USER_ADDRESS_STREET_2, USER_ADDRESS_STREET_3, USER_ADDRESS_CITY, USER_ADDRESS_STATE, USER_ADDRESS_COUNTRY, USER_ADDRESS_ZIP, USER_LOGIN_NAME, OLD_PASSWORD, NEW_PASSWORD | none | update information for specified user |
| update_lab_info | LAB_ID, LAB_ORGANIZATION_NAME, LAB_LAST_NAME, LAB_FIRST_NAME, LAB_MIDDLE_NAME, LAB_TITLE, LAB_PHONE, LAB_FAX, LAB_E_MAIL, LAB_ADDRESS_STREET_1, LAB_ADDRESS_STREET_2, LAB_ADDRESS_STREET_3, LAB_ADDRESS_CITY, LAB_ADDRESS_STATE, LAB_ADDRESS_COUNTRY, LAB_ADDRESS_ZIP, LAB_LOGIN_NAME, OLD_PASSWORD, NEW_PASSWORD | none | update information for specified lab |
| auth_emodel_retv | USER_LOGIN_NAME, USER_PASSWORD, E_MODEL_ID | E_MODEL_ID, FILESERV_IP, FILESERV_PORT or AUTHORIZATION DENIED | determine whether user owns specified emodel |
| auth_login | USER_LOGIN_NAME, USER_PASSWORD | PASSWORD_INCORRECT, or AUTHORIZED, or LOGIN_NAME_INCORRECT | determine whether user account exists, password correct |

Figure 14:
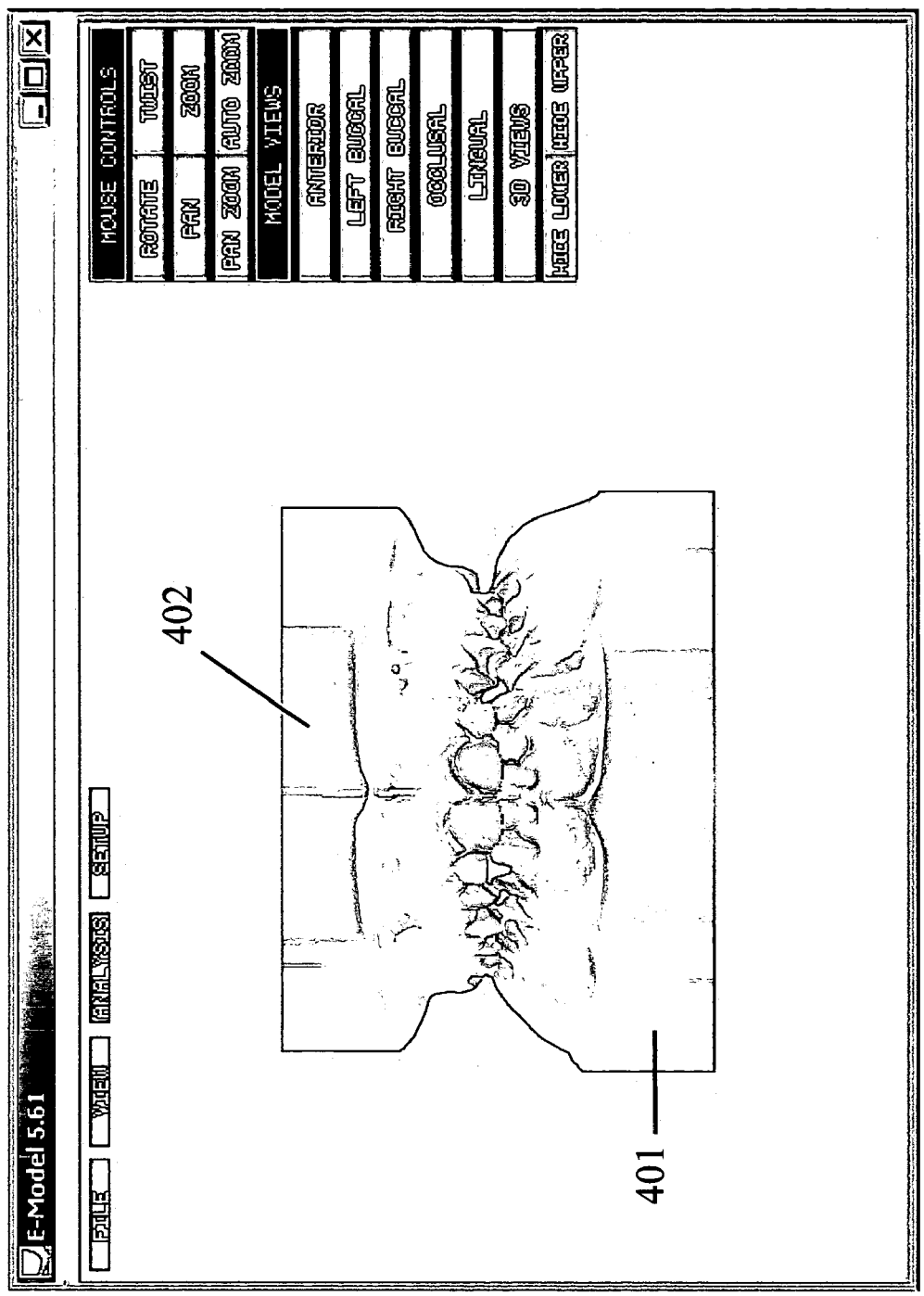
FIG. 14 illustrates an eModel for an impression of a patient's mouth according to yet another example embodiment of the present invention.

FIG. 14 illustrates an eModel for an impression of a patient's mouth according to yet another example embodiment of the present invention. In this example, the upper portion of the eModel 402 has been electronically moved and placed in its position above the lower portion of the eModel 401. The plaster models typically used in the dental care industry includes a base that allows easy spatial registration of the two portions of the eModel. This registration allows an end user to manipulate the parts of the eModel to observer and determine how the individual teeth interact as the two parts move together and apart from each other. The end user 110 may manipulate the eModel by moving, rotating and zooming to a perspective of interest.

Figure 15A:
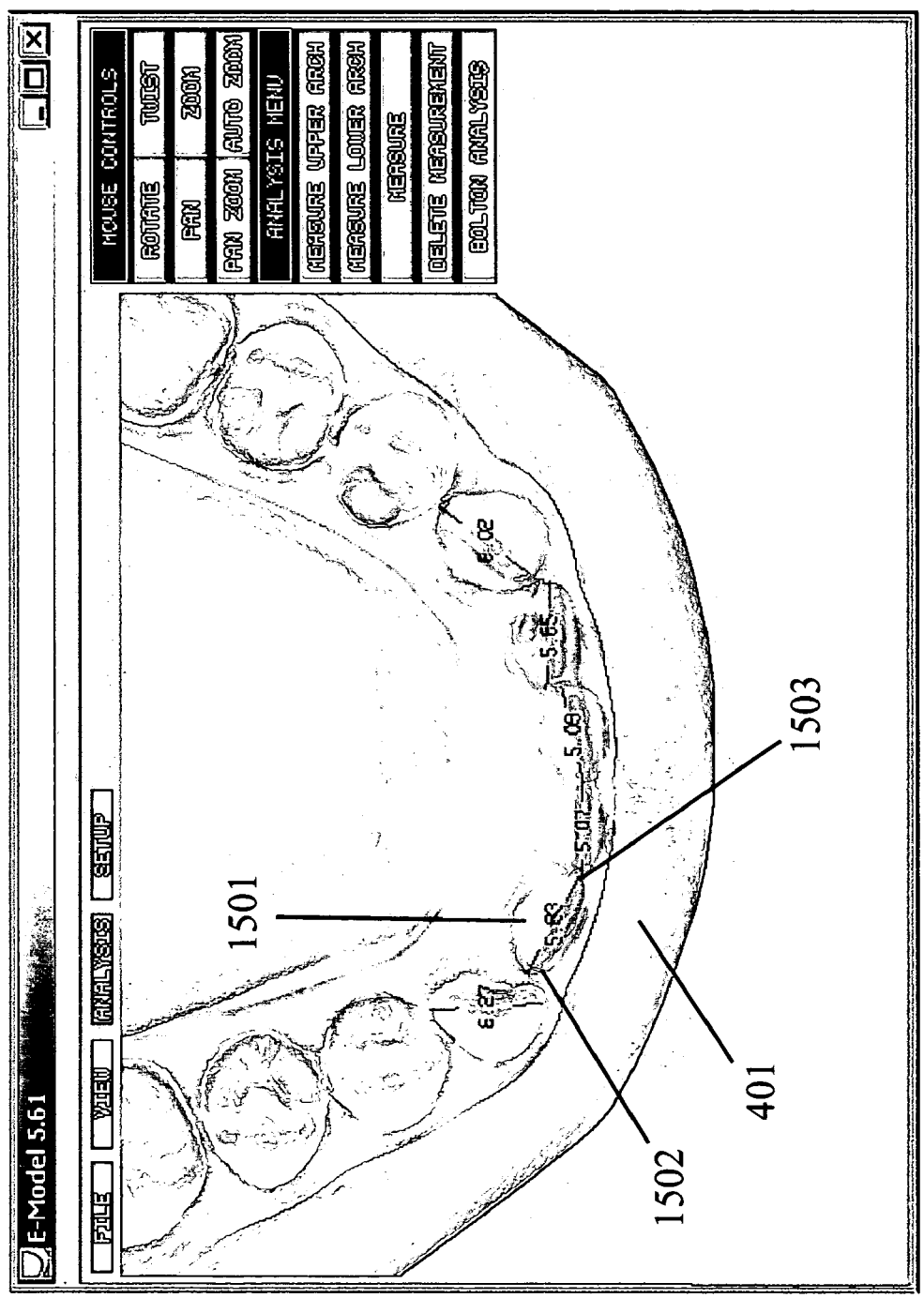
FIGS. 15a–b illustrate use of an eModel to determine spatial measurements corresponding to distances in a patient's mouth according to an embodiment of the present invention.
Figure 15B:
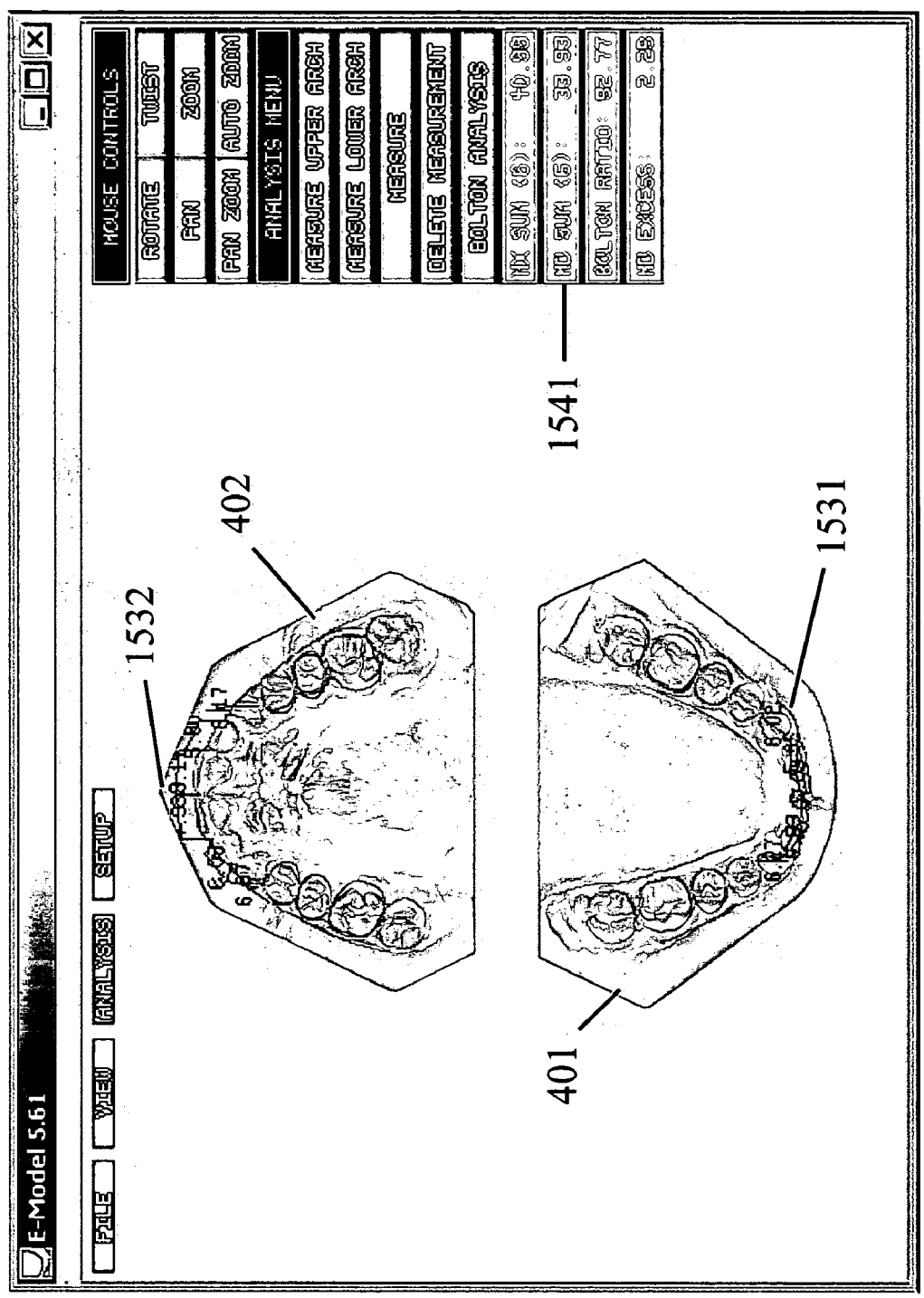

FIGS. 15a–b illustrate use of an eModel to determine spatial measurements corresponding to distances in a patient's mouth according to an embodiment of the present invention. In FIG. 15a, a zoomed view of a lower portion of the eModel 401 is shown in which individual spatial measurements of a tooth 1501 is determined by a user visually marking a first side of a tooth 1502 using an input device such as a mouse and/or a trackball. Next the end user marks a second side 1503 of the tooth 1501 and the end user client system determines the distance between the two points as measured on the eModel polygonal mesh surface. This process may be repeated as many times as desired. In the past, the dental plaster model would be measured to obtain these values. The end user system may automatically calculate this information, more accurately without the need to maintain and use the physical models once a eModel has been scanned, generated and saved.

FIG. 15b illustrates a similar set of spatial measurements being obtained for a series of teeth 1531 on the lower portion of the model 401 as well as a series of teeth 1532 on the upper portion of the model 402. These measurements 1531–1532 are typically used by dental care providers to determine a series of calculated values 1541 associated with the parabolic shape of a patient's mouth and teeth. The end user system may determine these values automatically from the spatial data measured by an end user that in the past would have required a significant amount of effort to obtain the measurements 1511–1512 and then calculate the values 1513.

Figure 16A:
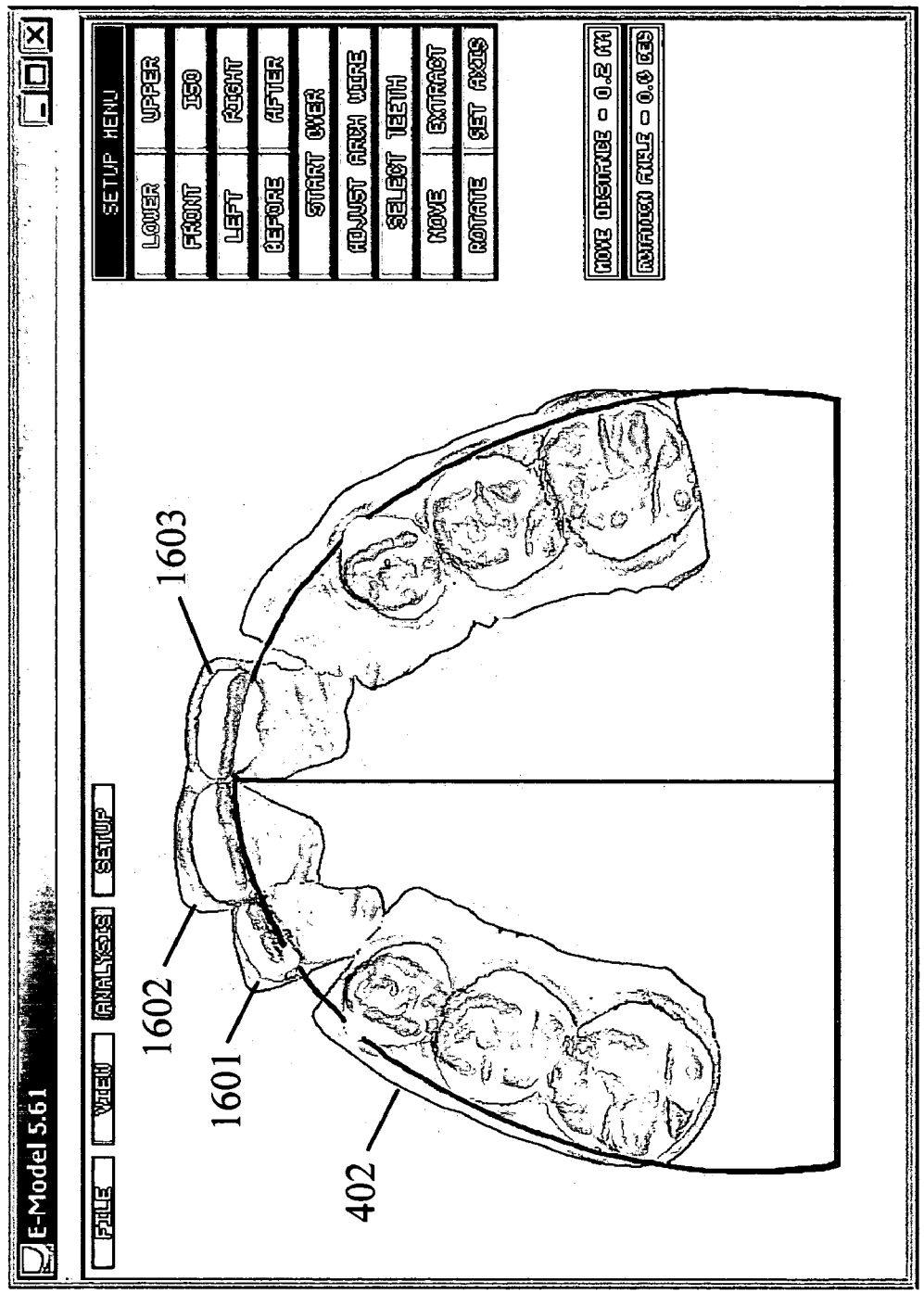
FIGS. 16a–b illustrate manipulating positions of patient's teeth using an eModel according to yet another example embodiment of the present invention.
Figure 16B:
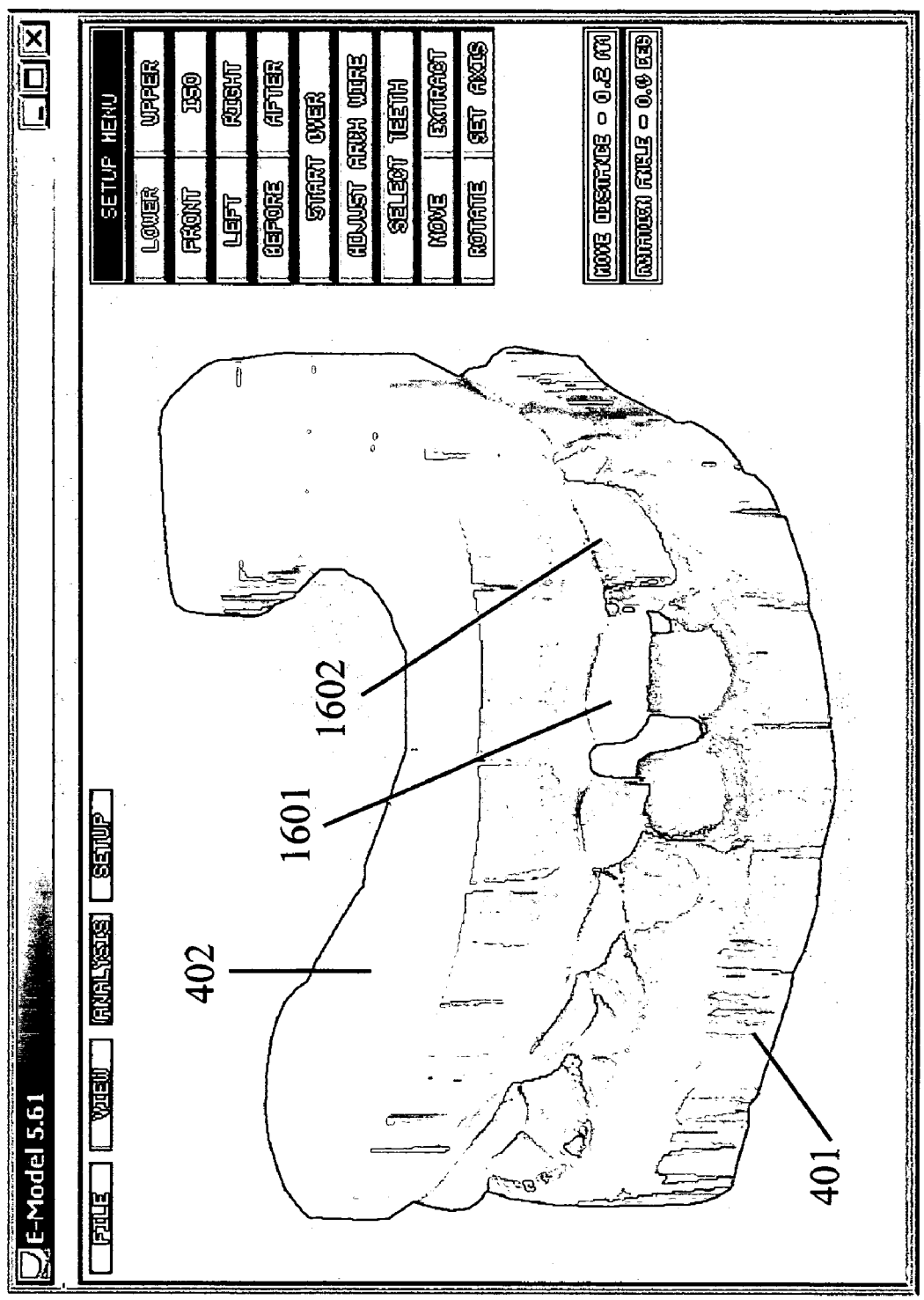

FIGS. 16a–b illustrate manipulating positions of patient's teeth using an eModel according to yet another example embodiment of the present invention. End users may be able to perform desired functions upon eModels that were difficult, or possibly impossible, to be performed upon physical models. FIG. 16a illustrates an upper portion of an eModel of a patient's teeth and mouth from a physical model obtained before dental treatment is performed. In this example, the dental care provider wishes to move the location of a number of teeth to better align them with the parabolic arc that human teeth are typically aligned. The dental care provider, as an end user of the system, selects and manipulates the location of three upper teeth 1601–1603 from a current position to a desired position.

The end user interactively moves portions of the eModel that represent the desired teeth to a new position. The dental care provider may remove teeth to determine spacing of the remaining teeth as a course of treatment for a patient is created. All of the possible variations on treatment options may be explored using the eModel until a desired course of treatment is determined.

FIG. 16b illustrates a different view for the eModel after the top front teeth 1601–1602 have been moved as shown in FIG. 16a. A new eModel for an item, such as the dental models, may be created through the modification of an existing eModel. Once the new model exists, it may be viewed and manipulated in the same manner as any other eModel. Thus the various possible views of the original eModel may be viewed once a new eModel has been created. In addition, an end user may toggle between the two models to illustrate a before and after view of the teeth in light of a proposed treatment plan. All of this treatment planning which has occurred with physical models and paper and pencil calculations may now be performed using the end user computing system.

Figure 17A:
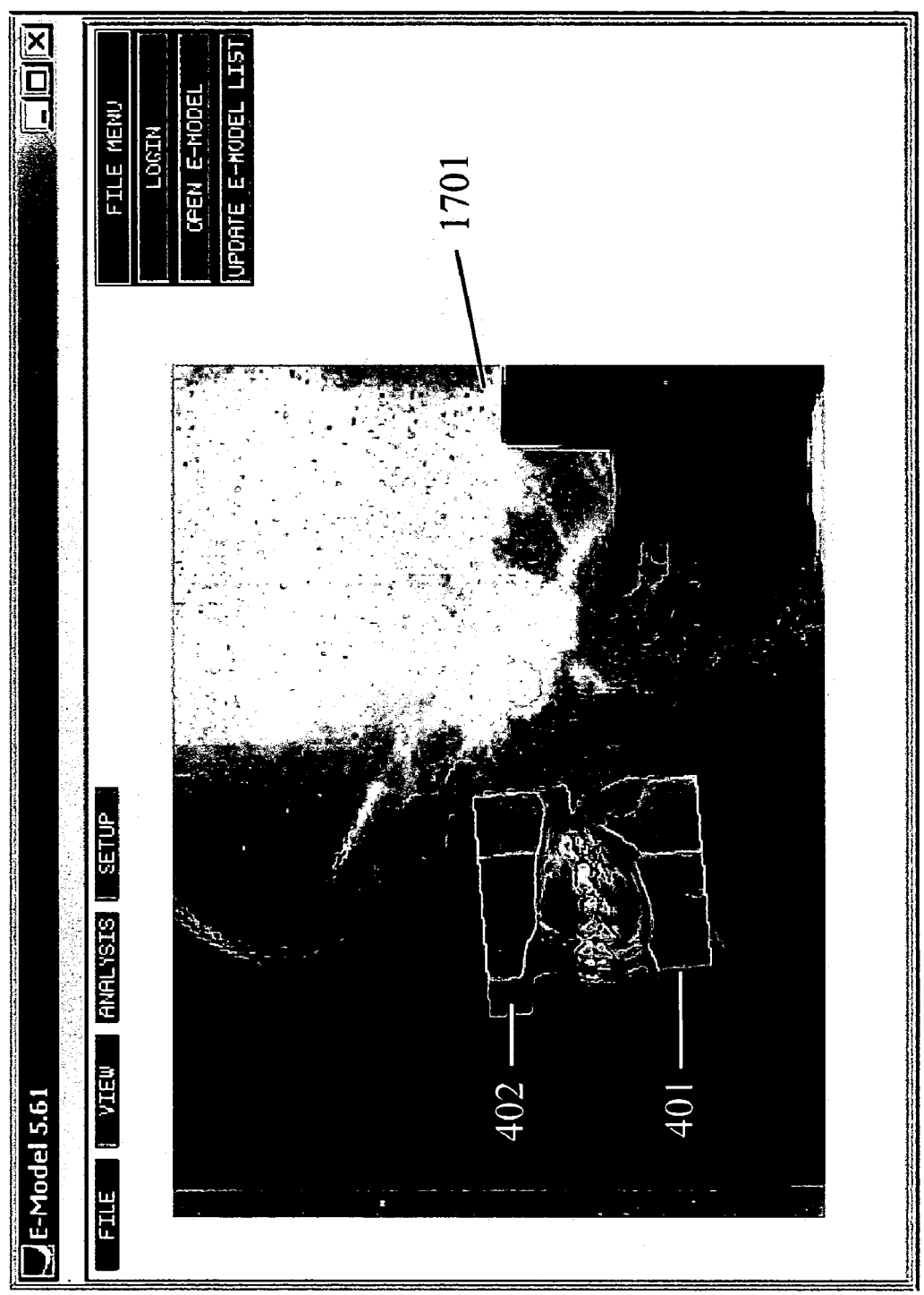
FIGS. 17a–c illustrate combining an eModel of a patient's teeth with an x-ray according to yet another example embodiment of the present invention.
Figure 17B:
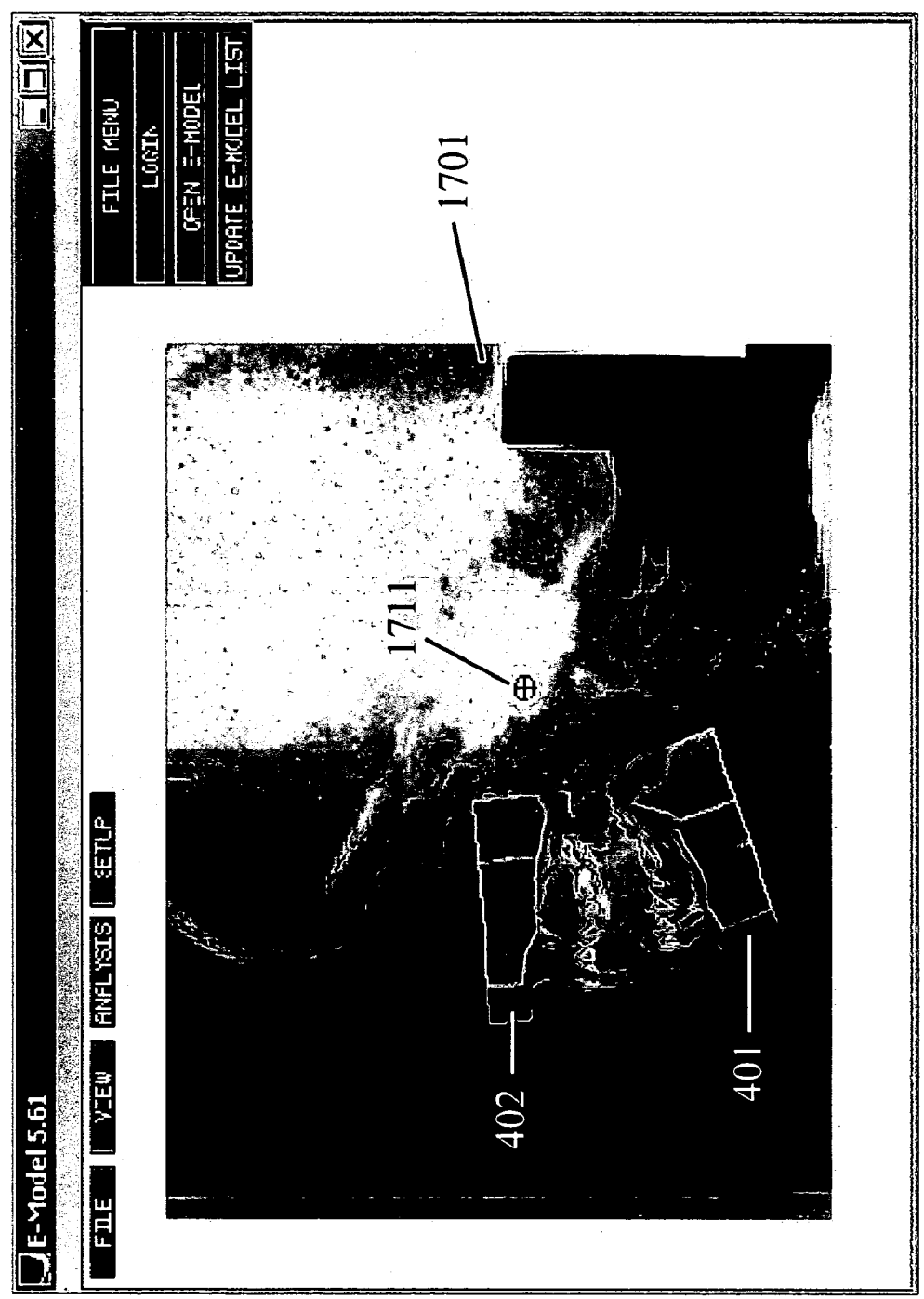
Figure 17C:
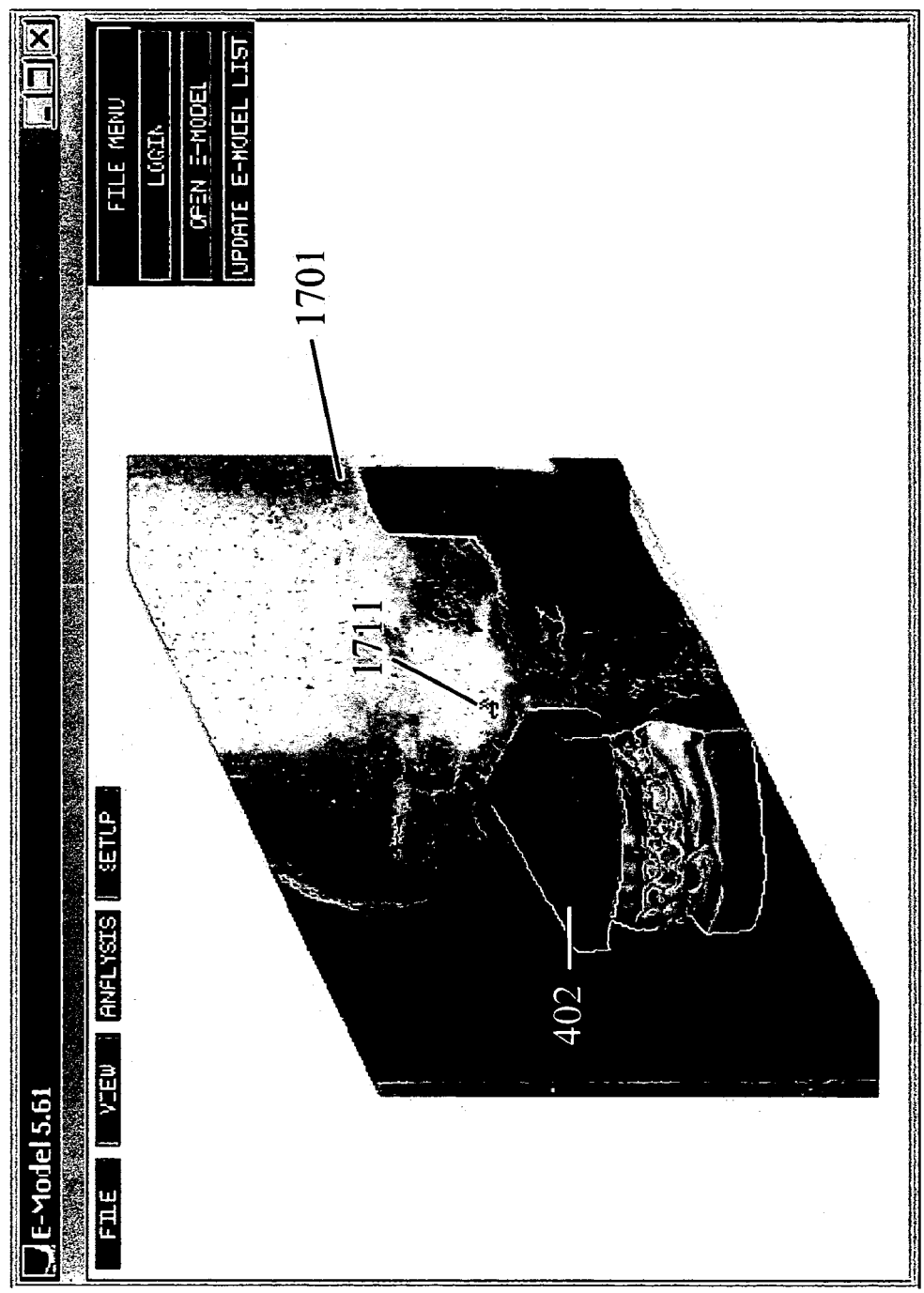

FIGS. 17a–c illustrate combining an eModel of a patient's teeth with an x-ray according to yet another example embodiment of the present invention. Even more significant than the simple manipulation of eModels, new types of eModels can be created that combine more than one form of digital image data to create a composite digital representation of patient data. FIG. 17a illustrates a combination of a scanned eModel of a patient's teeth 401–402 that has been combined with a corresponding x-ray image 1701 for the patient. In this example, a profile of the entire scull is viewed in the x-ray image 1701. The two digital modules, for the teeth 401–402 and for the x-ray 1701, both typically possess common reference points from the tips of various teeth and similar structures. When these common points are identified in both models, the processing system can register and scale the two models to permit the combination of these two different models into a single module.

Like above, once a new eModel is created, the new eModel may itself be manipulated. FIG. 17b illustrates the movement of a patient's lower jaw and teeth about the lower jaw pivot point 1711. As this movement occurs, the upper portion of the teeth eModel 402 and the lower portion of the teeth eModel 401 may be observed. As such, additional considerations may be viewed while a treatment plan is determined for a patient.

FIG. 17c further illustrates the possible options as the composite eModel 1701 has been rotated to display more of a frontal view of the teeth eModels 401–402 in combination with the x-Ray. One skilled in the art will recognize that numerous variations on the types of x-rays and other digital image data, including but not limited to digital photographs and textual annotation, that may be combined with scanned eModels to obtain an image based eModel-processing system without deviating from the spirit and scope of the present invention as recited within the attached claims.

Figure 18:
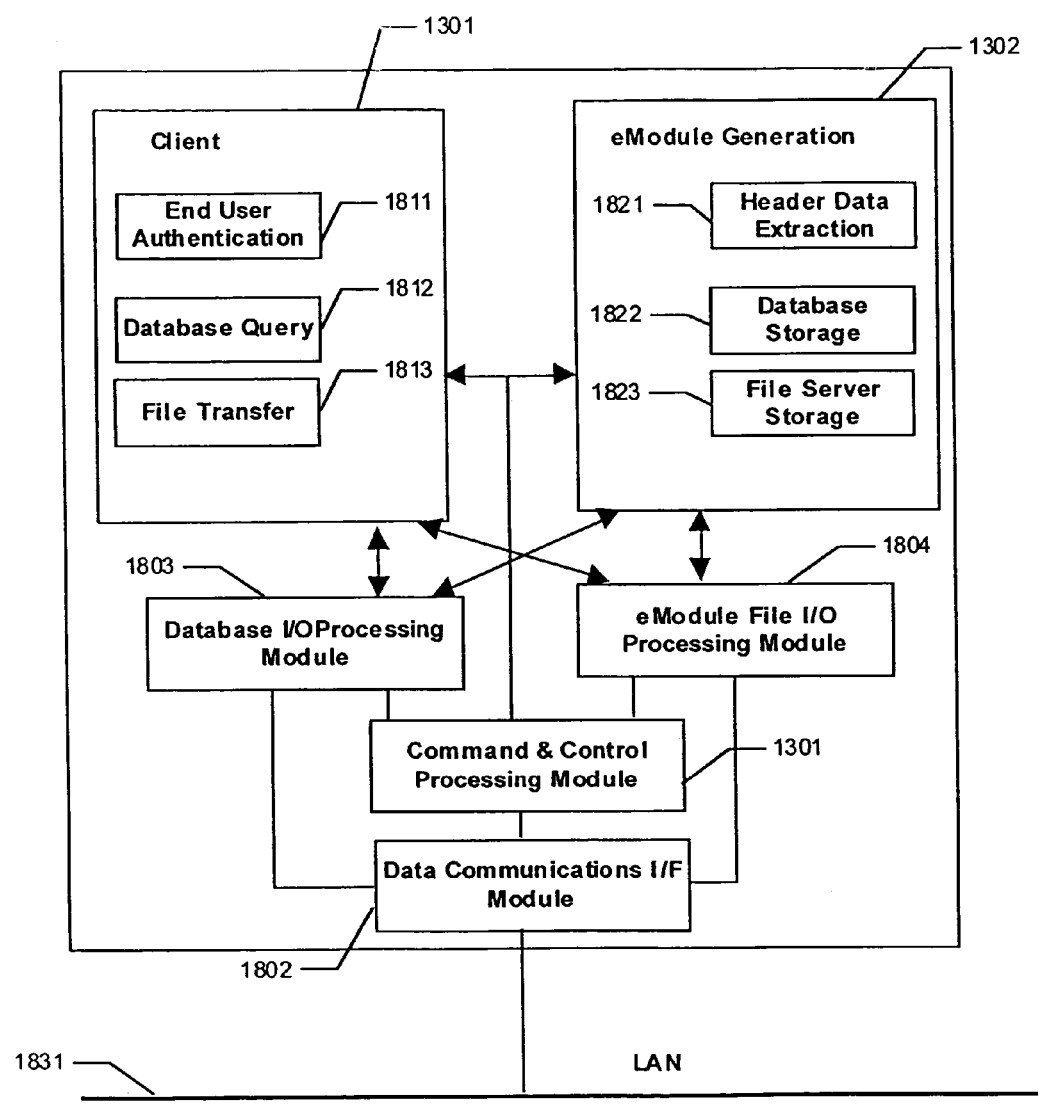
FIG. 18 illustrates processing modules used to implement an eModel data server according to an embodiment of the present invention.

FIG. 18 illustrates processing modules used to implement an eModel data server according to an embodiment of the present invention. As discussed in FIG. 13, the eModel server includes a communications server 1201 that has a client interface module 1303, an eModel generation interface module 1302, and a command and control-processing module 1301. In addition, the communications server 1201 includes a data communications interface module 1802 to perform processing functions needed to send and receive data communications to and from other processing modules over the local area network 1831. The command and control processing module 1301 receives requests for data operations and interacts with either a database I/O processing module 1803 or an eModel file I/O processing module 1804 to complete the processing. The database I/O processing module 1803 is responsible for all database query requests that occur when end users search for eModels of interest. The database I/O processing module 1803 also is responsible for storing new information into the relational database. The eModel file I/O processing module 1804 is responsible for storing eModels into the file storage database and for transferring stored eModels to end users.

The client interface module 1301 consists of an end user authentication module 1811, a database query module 1812, and a file transfer module 1813. The end user authentication module 1811 processes all end user attempts to log into the server to search for and access eModels. The database query module 1812 processes all incoming search requests to generate and process relational database queries to locate matching eModels based upon file header info data. The file transfer module 1813 processes all eModel transfer requests to send eModels to end-users.

The eModel generation interface module 1302 processes all commands to store new eModels generated in the eModel generation system into the data server. The eModel generation interface module 1302 includes a header extraction module 1821, a database storage module 1822, and a file server storage module 1823 to complete its functions. The header extraction module 1821 extracts the file header info data from incoming eModels and formats them for insertion into the relational database. The database storage module 1822 stores the formatted header data into the relational database as needed to permit easy and efficient searches. The file server storage module 1823 performs the operations needed to store the eModels into the file storage server.

Figure 19:
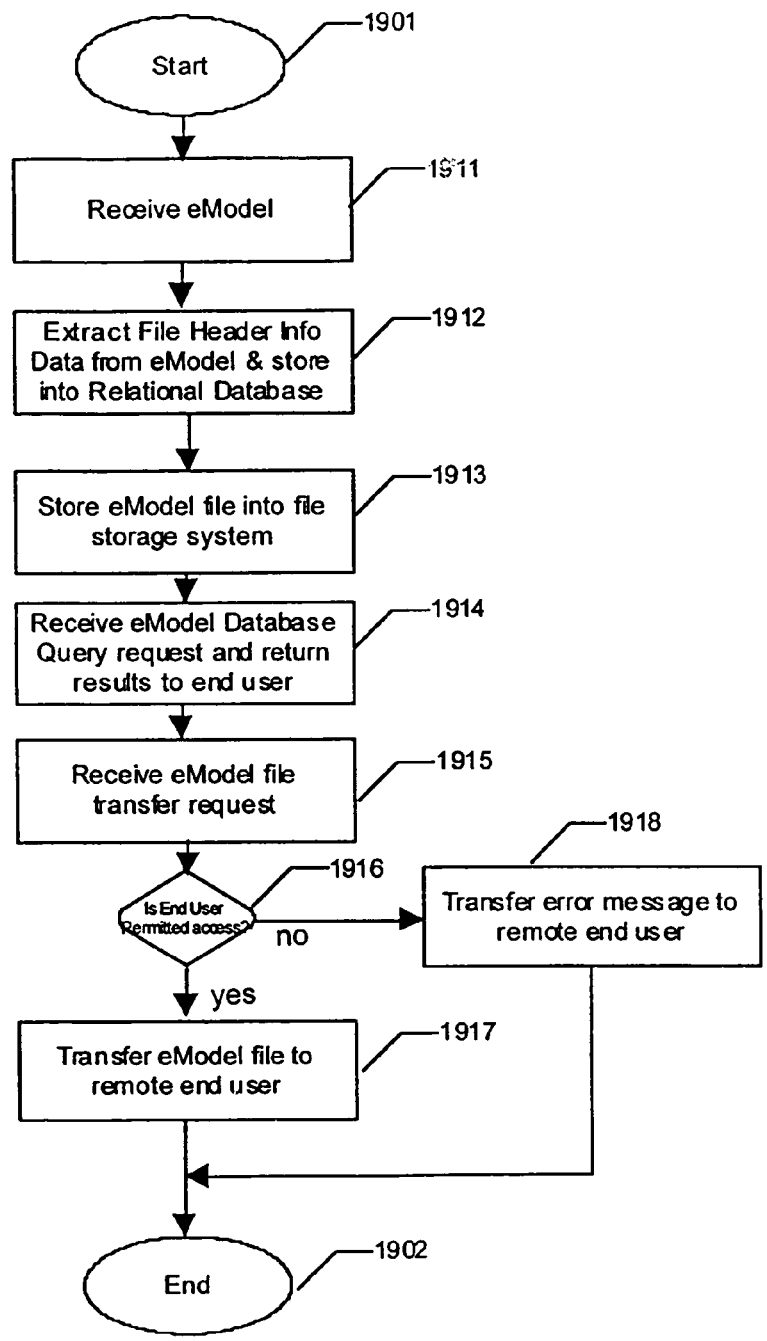
FIG. 19 illustrates an operational flow for the processing performed within an eModel data server according to yet another example embodiment of the present invention.

FIG. 19 illustrates an operational flow for the processing performed within an eModel data server according to yet another example embodiment of the present invention. The process starts 1901 and the data server receives an eModel in module 1911 after it has been generated in some manner. One a new eModel has been received, module 1912 extracts a file header info data from the eModel file. This module 1912 formats this information and necessary and stores it into a searchable relational database for use in locating the corresponding eModel at a later date.

Next, the server stores the eModel file into a file storage server in module 1913 in order to allow the eModel to be retrieved by end users. The end users locate the eModels by submitting a query to the relational database to perform a search on the file header info data. The server receives the query request in module 1914 which causes the module 1914 to query the relational database and return the query results to the end user. The end user next sends a request for additional queries if necessary to identify any eModels of interest.

Once the end user has identifies a desired eModel, the end user sends a request for an eModel to the data server which is received in module 1915. Test module 1916 determines if the end user is permitted access to the requested eModel. If access is permitted, the eModel is transferred to the end user by module 1917 and the processing ends. If test module 1916 determines that access to the eModel is not permitted, the error message is returned to the end user by module 1919 and the processing also ends. One skilled in the art will recognize that alternate user authentication and access authorization mechanisms may be used to limit access to end users when database queries are made as well as when eModels are accessed without deviating from the spirit and scope of the present invention as recited within the attached claims.

Figure 20:
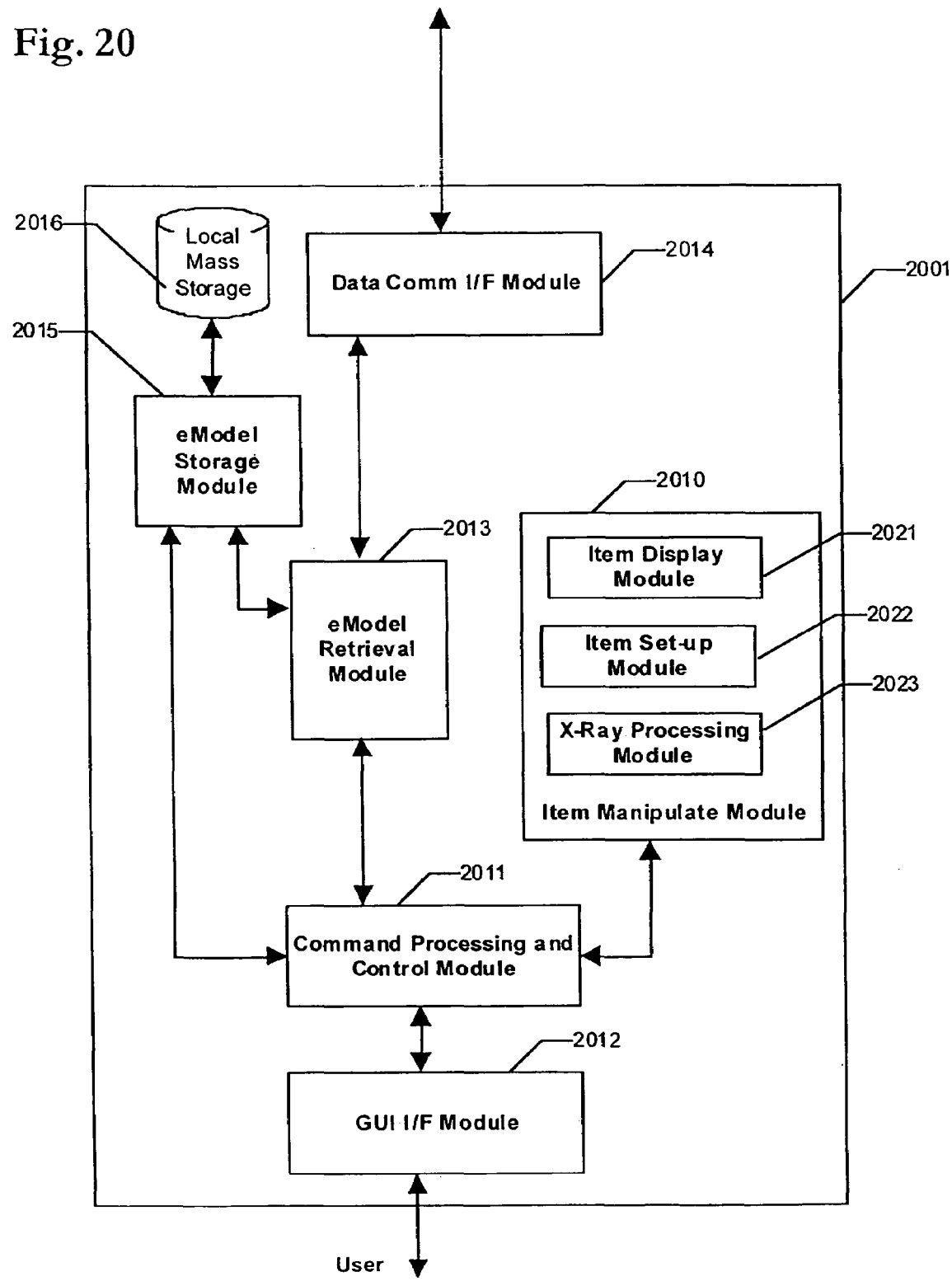
FIG. 20 illustrates processing modules used to implement an end user client computer according to yet another example embodiment of the present invention.

FIG. 20 illustrates processing modules used to implement an end user client computer according to yet another example embodiment of the present invention. The end user client computer includes a set of processing modules to provide a window-based user environment to interact with eModels. The client computer 2001 includes a graphical user interface (GUI) module 2012, a command processing and control module 2011, an eModel Item Manipulate module 2010, an eModel storage module 2015, an eModel retrieval module 2013, and a data communications interface module 2014. The client computer 2001 may also include local mass storage 2016 to maintain eModels locally as well as on the data server 102.

The end user interacts with the client computer 2001 through the GUI interface module 2012. The end user enters commands using a pointing device such as a mouse or trackball and using keyboard commands. These commands are processed by the command processing and control module 2011 which send processing requests to the other modules to complete the requested command.

Commands to view an eModel is processed by the eModel retrieval module 2013. The eModel retrieval module 2013 obtains a list of the locally available eModels from the eModel storage module 2015 as well as communicates with the remote data server 102 using the data communications interface module 2014. The end user is presented with a list of available eModels from which an eModel is selected and retrieved. The eModel is retrieved from local storage 2016 if available. If not, the eModel may be transferred from the remote storage. If desired, the retrieved eModel may be stored locally when retrieved from the remote server to eliminate the need to down load the eModel in the future. Of course, the eModels may also be stored only upon the remote data server 102 and retrieved when needed.

Once an eModel has been retrieved from data storage, the eModel is processed within the eModel Item Manipulate module 2010. This module displays the eModel to the end user. The eModel Item Manipulate module 2010 includes an item display module 2021, an item set-up module 2022, and an x-Ray processing module 2023. The item display module 2021 displays the eModel graphically to the end user as well as performs the image display related manipulation operations such as zoom, pan, scroll, and similar visual operations. The item set-up module 2022 allows end users to obtain measurements of the eModel and modify the eModel to create new eModels that may be saved locally using the eModel retrieval module 2013. The x-Ray processing module 2023 performs the operations necessary to manipulate x-rays as well as combine them with other eModels to create and store composite eModels. One skilled in the art will recognize that additional manipulation modules may also be used to process commands associated with various composite eModels created using other supported digital image based eModels without deviating from the spirit and scope of the present invention as recited within the attached claims.

Figure 21:
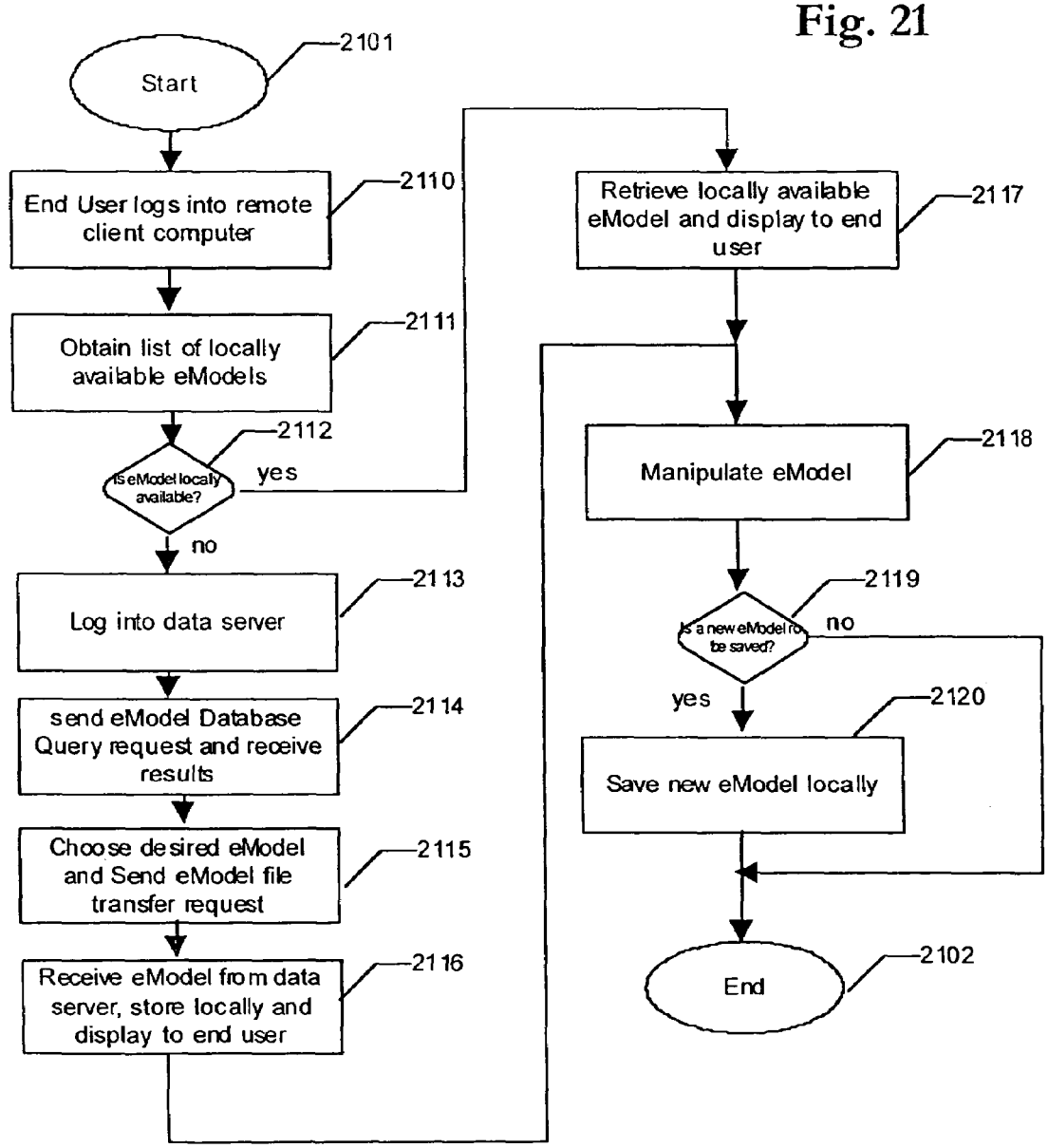
FIG. 21 illustrates an operational flow for the processing performed within an end user client computer according to yet another example embodiment of the present invention.

FIG. 21 illustrates an operational flow for the processing performed within an end user client computer according to yet another example embodiment of the present invention. The end user process starts 2101 and the end user logs into the client computer in module 2110. This logging in allows the client system to limit access to eModels if needed when the eModels represent confidential data, such as patient data, to only users who are trusted to use the data appropriately.

Once logged in, an end user is presented with a list of locally available eModels that were obtained in module 2111. Test module 1212 determines if a desired eModel is available locally. If test module 1212 determines that the desired eModel is not available, the client computer logs into a remote data server in module 2113 to locate the desired eModel. A database query used to locate the desired eModel is sent to the remote server in module 2114 before receiving a list of remotely available eModels. The end user selects the desired eModel and sends a request for the remotely available eModel to be transmitted to the client computer in module 2115. The client computer receives the eModel from the remote server, stores it locally, and displays it to the user for manipulation in module 2118.

If test module 2112 determines the desired eModel is locally available, the eModel is retrieved and displayed to the user in module 2117 before a user manipulates it in module 2118. The end user interactively manipulates the eModel as needed in module 2118 to perform the analysis and planning functions that the eModel is useful is assisting. Test module 2119 determines if a new eModel has been created that an end user wishes to save locally. If a new eModel is to be saved, module 2120 will save the newly created eModel locally before the processing ends 2102. If module 2119 determines that a new eModel is not to be saved, the processing ends immediately 2102.

FIGS. 22–26 illustrate an implementation of the concepts described herein pertaining to dental restorations, for example dental crowns and dental implants. An eModel of a proposed dental restoration for a patient can be created in the manner discussed above, typically by a dental restoration lab. The restoration eModel can then be combined with an eModel of the remainder (or a finite) portion of the patient's teeth at the location where the proposed restoration is to be placed, thereby creating a dental restoration treatment eModel. The treatment eModel can then be sent to the patient's doctor, who can then view the proposed restoration relative to neighboring teeth and analyze whether or not the restoration is suitable. If the proposed restoration is acceptable, the doctor can deliver the treatment eModel to the dental restoration lab for fabrication of the actual dental restoration. If the proposed restoration is not acceptable, the doctor can take suitable action and notify the restoration lab that the proposed restoration needs to be revised.

Figure 22:
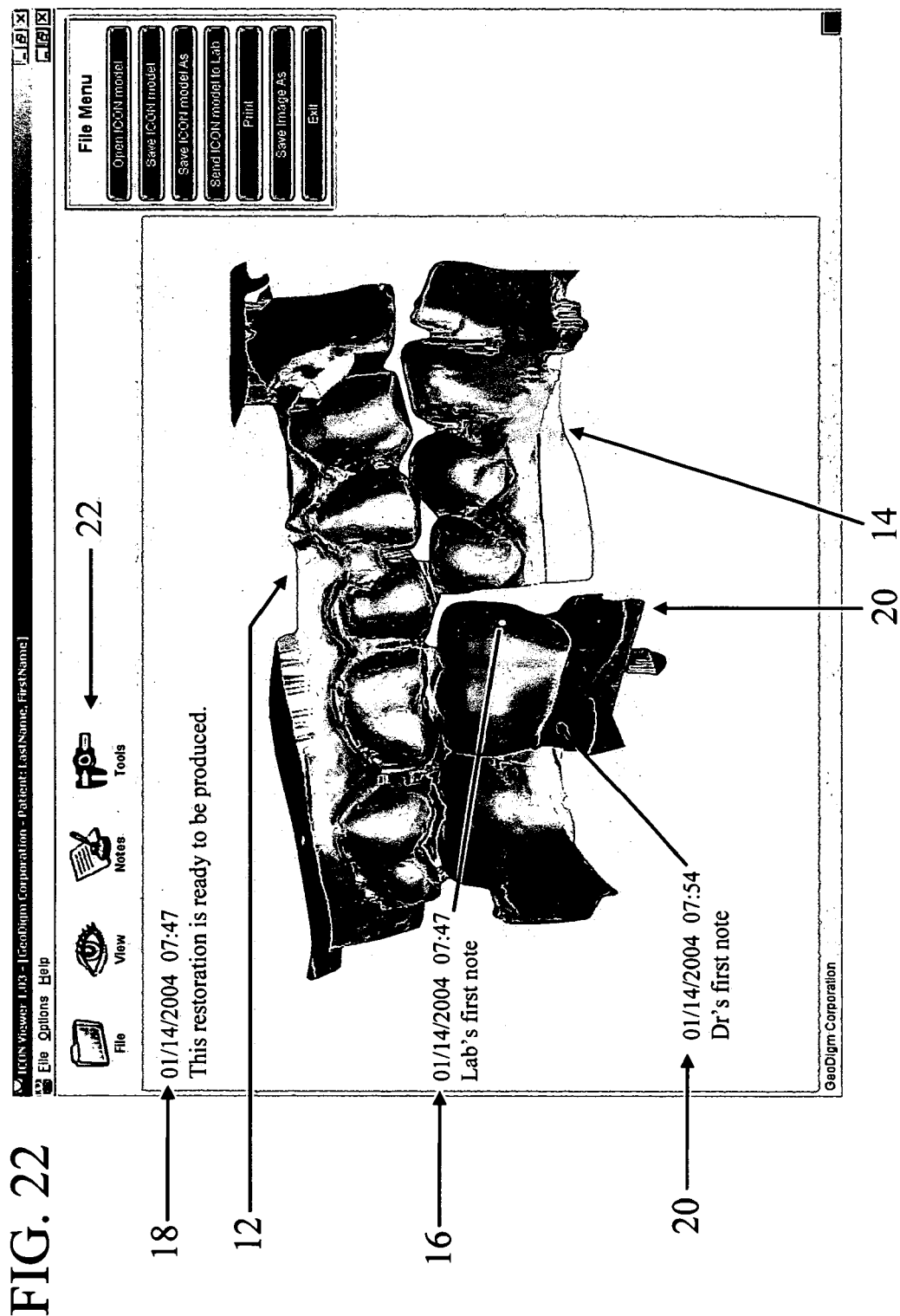
FIGS. 22–26 illustrate end user display screens on an end user client computer for use in viewing and manipulating a dental restoration eModel according to an embodiment of the present invention.

FIG. 22 illustrates a display screen of a doctor's computer or any other computer to which the doctor may decide to utilize for analyzing treatment eModels. The screen displays a proposed dental restoration 10 eModel comprising a combination of a crown and a prep site and/or implant. The restoration 10 eModel is shown in its intended location relative to upper 12 and lower 14 eModels of the patient's teeth. Together, the restoration 10 eModel and the eModels 12, 14 form a dental restoration treatment eModel. The treatment eModel is typically generated at a location remote from the doctor, for example by a dental restoration lab. The treatment eModel is stored within computer readable memory as discussed above. The treatment eModel can then be delivered to the doctor for analysis of the proposed dental restoration.

Notations can be attached to the treatment eModel as a means of communication between the lab and the doctor. For example, FIG. 22 shows a notation 16 added by the lab commenting on a particular portion of the proposed restoration 10, along with a notation(s) added by the lab 18 indicating to the doctor that the proposed restoration 10 is ready to be fabricated once the doctor gives the go ahead. A notation(s) 20 can also be added by the doctor to comment on any particular portion of the proposed restoration 10. It will be appreciated that more than one doctor can add notations and the lab can similarly add notations.

Along the top of the display screen are icons 22 that allow the doctor to select different menus of tools for use in displaying and analyzing the restoration. FIG. 22 shows the file menu tools that open when the doctor clicks on the "File" icon, permitting the doctor to perform any of the operations listed under the file menu.

Figure 23:
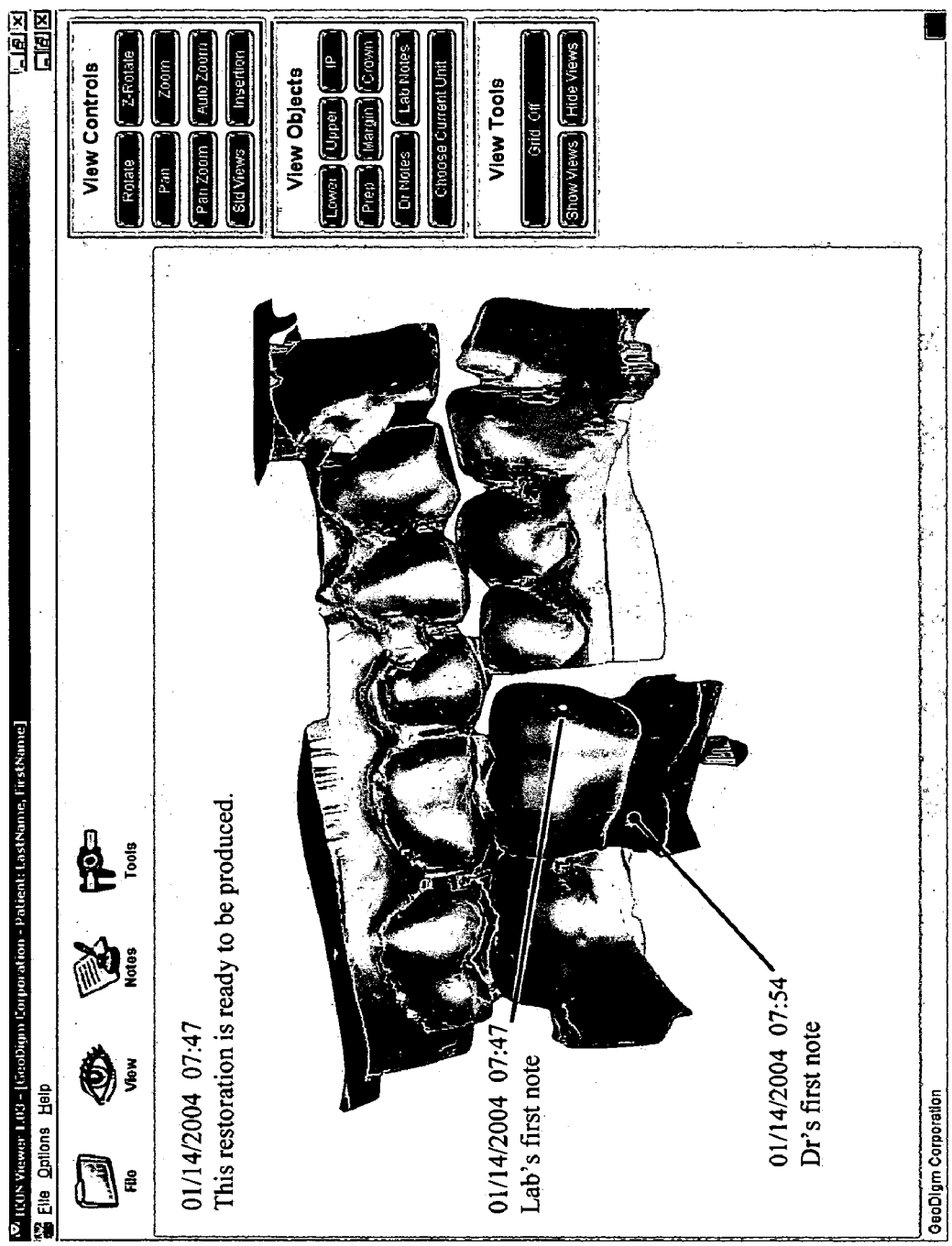

FIG. 23 shows the display screen that results when the doctor clicks on the "View" icon, permitting the doctor to perform any of the operations listed under the menus. The operations include the ability to manipulate the treatment eModel, including changing the view orientation of the eModel (View Controls), as well as selecting the elements of the eModels that are displayed (View Objects) and selecting tools (View Tools) to aid in analyzing the proposed restoration 10.

Figure 24:
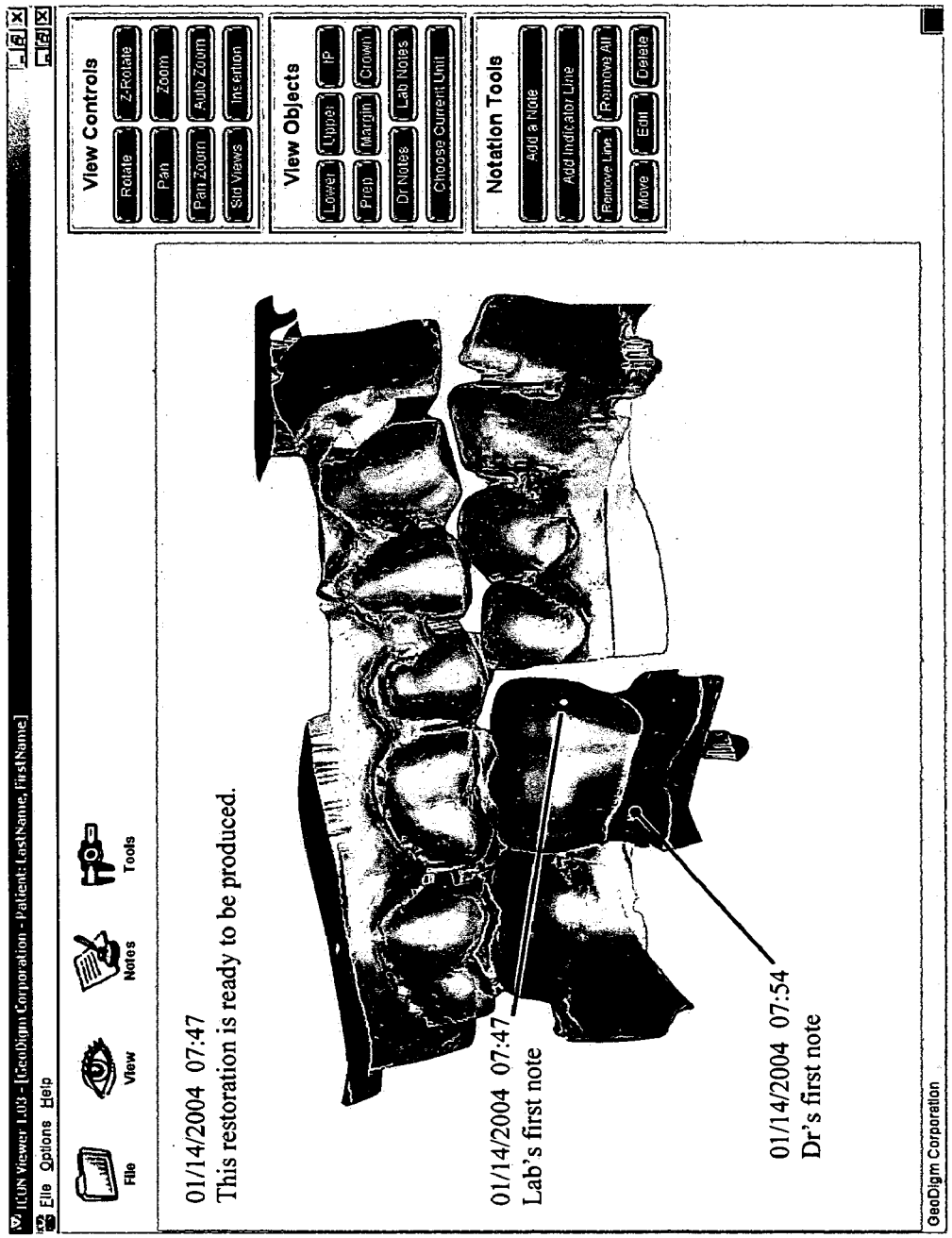

FIG. 24 shows the display screen that results when the doctor clicks on the "Notes" icon, permitting the doctor to perform any of the operations listed under the menus. In addition to View Controls and View Objects menus, the doctor is presented with a Notation Tools menu that allows the doctor to add, remove, move and edit notations 20 on the treatment eModel. Notations allow the doctor to comments on areas of the treatment eModel that may need to be altered to optimize the restoration, so that when the treatment eModel with attached notation is sent back to the lab, the lab technician knows which areas of the treatment eModel may need to be revised and by how much.

Figure 25:
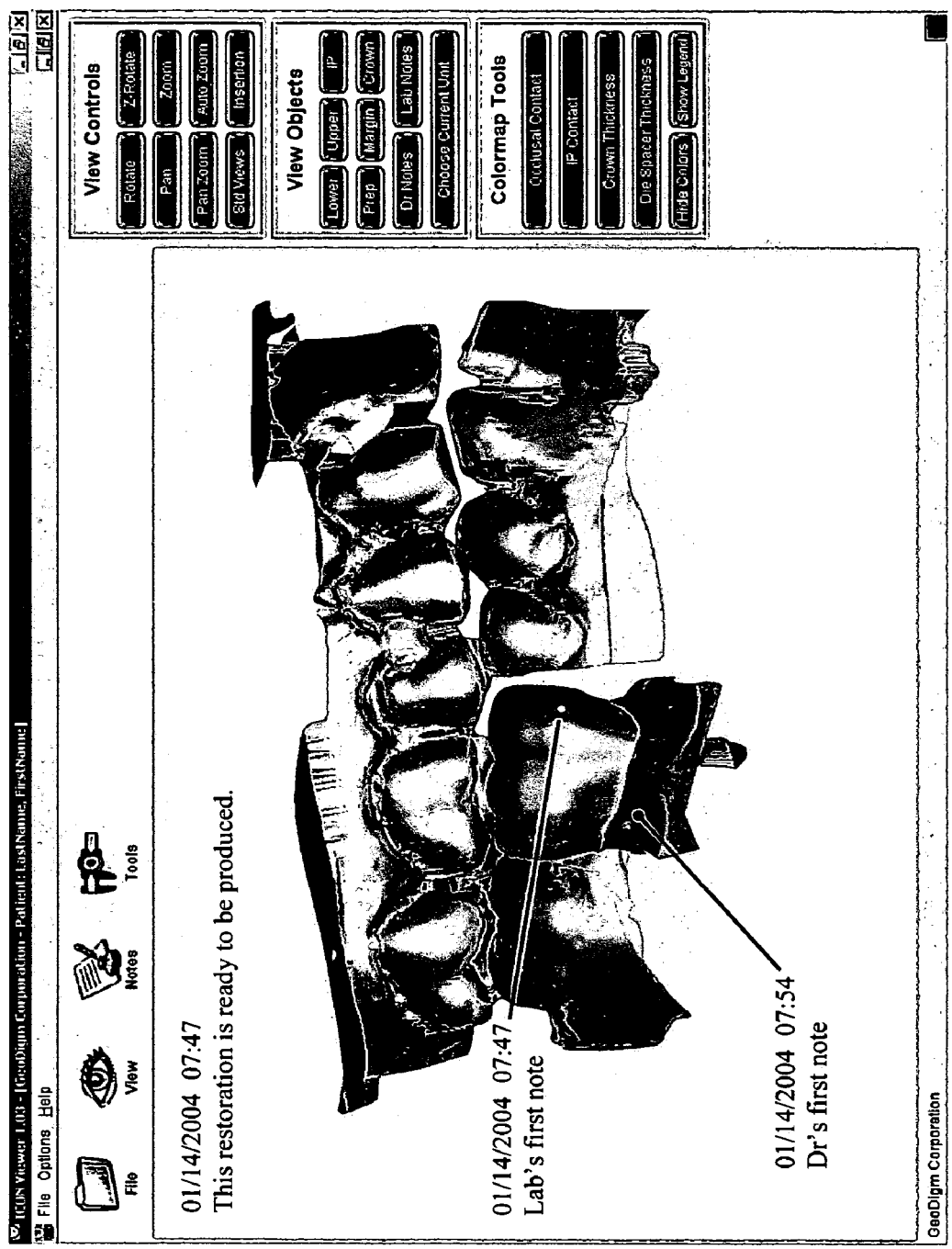

FIG. 25 shows the display screen that results when the doctor clicks on the "Tools" icon, permitting the doctor to perform any of the operations listed under the menus. In addition to View Controls and View Objects menus, the doctor is presented with a Colormap Tools menu that allows the doctor to analyze certain parameters relating to the interaction between the proposed restoration and neighboring teeth, and parameters of the proposed restoration itself. For example, the Colormap Tools menu enables the doctor to analyze occlusal contact, interproximal contact, thickness of the crown, and the thickness between the bottom of the crown and the top of the prep site or implant.

Figure 26:
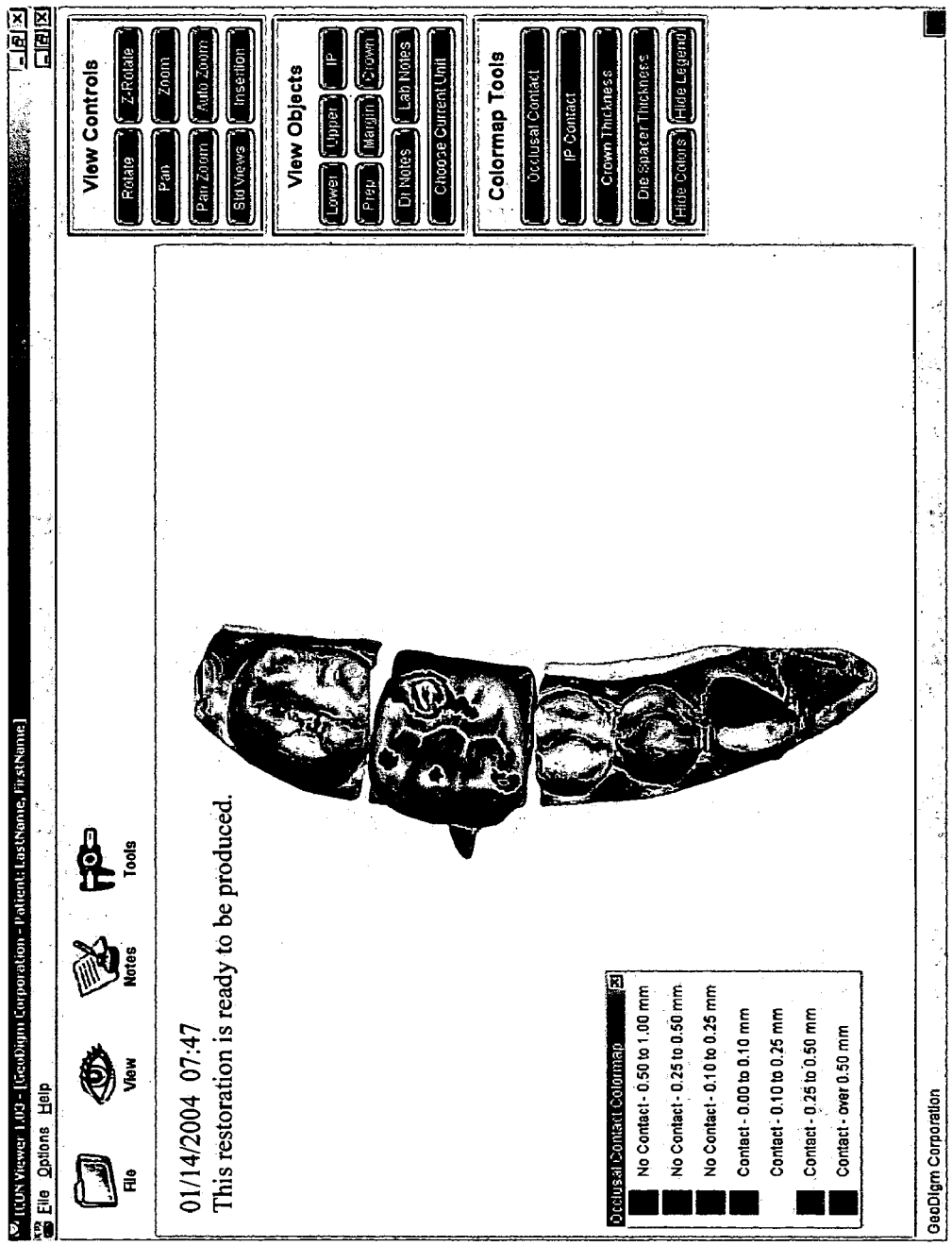

The Colormap Tools menu allows the doctor to display the locations of occlusal contact and the degree of contact as part of his analysis, as shown in FIG. 26, with different colors being used to represent differing degrees of contact, as indicated in the displayed legend.

Figure 27:
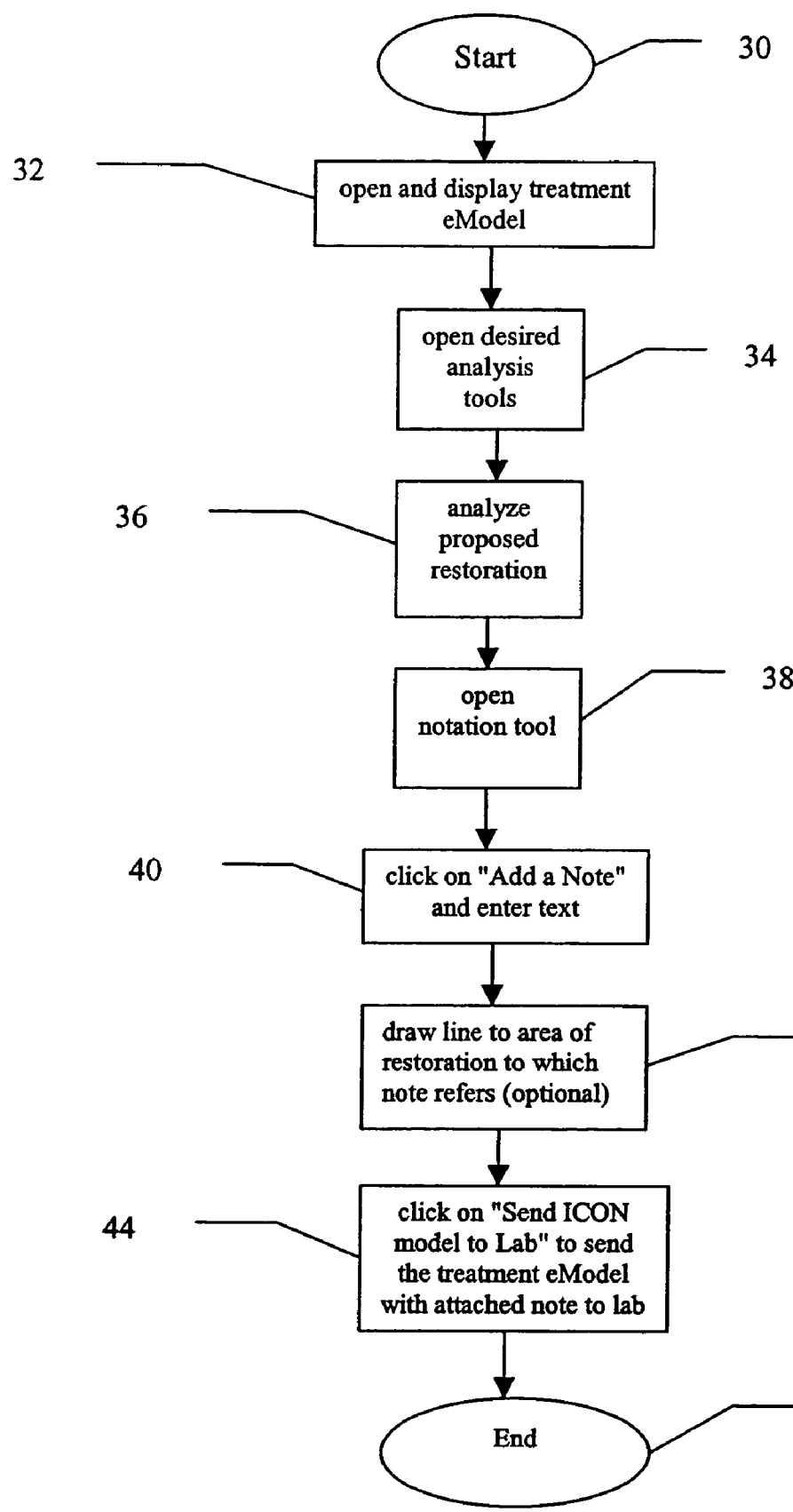
FIG. 27 illustrates an operational flow of an exemplary dental restoration treatment process using the dental restoration eModel.

FIG. 27 illustrates an operational flow of an exemplary dental restoration treatment process using the dental restoration eModel. The process starts 30 and the treatment eModel is opened and displayed 32 by the doctor after the treatment eModel has been sent to the doctor by the lab. The doctor opens 34 the desired analysis tools and analyzes 36 the proposed restoration to determine whether the proposed restoration is acceptable. If the proposed restoration is not acceptable, or the doctor simply wants to send a message to the lab, the doctor opens 38 the notation tool and clicks on "Add a Note" 40 and enters the text of the message. The doctor then optionally clicks on "Add Indicator Line" to draw a line to the area of the treatment eModel to which the note applies. If the note is not directed to a specific area of the treatment eModel, then an indicator line may not be necessary. Once all notes have been added and the doctor has completed the analysis, the doctor clicks on "Send ICON model to Lab" in the file menu to send the treatment eModel with the attached notes to the lab for consideration and revision of the eModel. The doctor can also save the treatment eModel, including the notes, on a suitable computer readable storage medium for later use. Once the eModel is sent back to the lab, that stage of the process ends 46.

The process in FIG. 27 can be iterative, in which case the lab can send the revised treatment eModel back to the doctor once revisions have been made for approval by the doctor. The doctor can make a further analysis and, if necessary, suggest further modifications, or, if no additional changes are necessary, approve the restoration for subsequent fabrication.

The software program (and programming steps) implementing the present invention is a single executable file stored and implemented by the end user's (e.g., the doctor) 110–113 computers. The program is written in C and C++. The program QT is utilized to make the Microsoft Windows calls to enable higher level/simplified coding. The program can alternatively be implemented as a browser based web service (for example using Java scripts).

FIG. 2 preferably illustrates an example of a suitable operating environment 121 in which the invention may be implemented. The operating environment is only one example of a suitable operating environment 121 and is not intended to suggest any limitation as to the scope of use or functionality of the invention. Other well known computing systems, environments, and/or configurations that may be suitable for use with the invention include, but are not limited to, personal computers, server computers, held-held or laptop devices, multiprocessor systems, microprocessor-based systems, programmable consumer electronics, network PCs, minicomputers, mainframe computers, distributed computing environments that include any of the above systems or devices, and the like.

The invention may also be described in the general context of computer-executable instructions, such as program modules, executed by one or more computers or other devices. Generally, program modules include routines, programs, objects, components, data structures, etc. that perform particular tasks or implement particular abstract data types. Typically the functionality of the program modules may be combined or distributed in desired in various embodiments.

A network server 121 typically includes at least some form of computer readable media. Computer readable media can be any available media that can be accessed by the network server 110. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, BC-ROM, digital versatile disks (DVD) or other optical storage, magnetic cassettes, magnetic tape, magnetic disk storage or other magnetic storage devices, or any other medium which can be used to store the desired information and which can be accessed by the network server 110.

Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media.

While the above embodiments of the present invention describe a network based processing system providing processing services to remote clients, one skilled in the art will recognize that the various distributed computing architectures may be used to implement the present invention as recited within the attached claims. It is to be understood that other embodiments may be utilized and operational changes may be made without departing from the scope of the present invention.

The foregoing description of the exemplary embodiments of the invention has been presented for the purposes of illustration and description. They are not intended to be exhaustive or to limit the invention to the precise forms disclosed. Many modifications and variations are possible in light of the above teaching. It is intended that the scope of the invention be limited not with this detailed description, but rather by the claims appended hereto. Thus the present invention is presently embodied as a method, apparatus, computer storage medium or propagated signal containing a computer program for providing a method, apparatus, and article of manufacture for providing a distributed computing system for the creation and distribution of electronic models of objects.

What is claimed is:

1. A method for providing electronic delivery of an electronic model image of a dental restoration treatment, the method comprising:
    generating an electronic model image of a proposed dental restoration treatment the proposed dental restoration treatment including an electronic model of a proposed dental restoration displayed over an electronic model of surrounding dentition;
    storing the electronic model image within computer readable memory of a server-based computing system;
    delivering the electronic model image to a doctor having a remote client computer over a network; and
    displaying the electronic model image upon the remote client computer and performing analysis of the electronic model image.

2. The method of claim 1, further comprising attaching a notation to the electronic model image and displaying the attached notation upon the remote client computer.

3. The method of claim 2, further comprising delivering the electronic model image with the attached notation to a dental restoration laboratory.

4. The method of claim 1, further comprising manipulating the displayed electronic model image upon the remote client computer.

5. The method of claim 1, further comprising storing the electronic model image within computer readable memory of the remote client computer.

6. A method of dental restoration treatment, comprising:
    displaying an electronic model image of a proposed dental restoration treatment upon a display device;
    performing an analysis of the electronic model image to determine whether or not the proposed dental restoration treatment is appropriate; and
    attaching a notation to the electronic model image that is displayed, the notation configured to be displayed upon the display device when the electronic model image is displayed.

7. The method of claim 6, further comprising delivering the electronic model image with the attached notation to a dental restoration laboratory over a network.

8. The method of claim 6, wherein the analysis comprises manipulating the displayed electronic model image.

9. The method of claim 8, wherein manipulating comprises changing the orientation of the displayed electronic model image.

10. The method of claim 8, wherein the analysis comprises determining and indicating an occurrence of occlusal contact between a dental restoration and surrounding teeth shown in the electronic model image.

11. The method of claim 8, wherein the analysis comprises determining an occurrence of interproximal contact with a dental restoration of the proposed dental restoration treatment.

12. The method of claim 6, further comprising storing the electronic model image with the attached notation within computer readable memory.

13. A method comprising:
    obtaining a first electronic model of a proposed dental restoration treatment, the first electronic model including an electronic model of a dental restoration superimposed over an electronic model of surrounding dentition;
    delivering the first electronic model from a first computer to a second computer over a network;

receiving at the first computer the first electronic model from the second computer, the first electronic model including a first attached notation; and displaying the first electronic model on the first computer including displaying the first attached notation superimposed over the first electronic model.

14. The method of claim 13, further comprising:

manipulating the first electronic model based on the first attached notation;

saving the first electronic model on the second computer; and delivering the first electronic model to the first computer over the network.

15. The method of claim 13, further comprising attaching a second notation to the first electronic model, the second attached notation being displayed superimposed over the first electronic model with the first attached notation.

16. The method of claim 15, wherein attaching a second notation comprises:

indicating a selection to add a notation to the first electronic model;

inputting text referring to the first electronic model;

displaying the text superimposed over the first electronic model; and storing the text with the first electronic model.

17. The method of claim 15, wherein attaching a second notation further comprises drawing an indicator line from the text to an area of the first electronic model to which the text refers.

18. The method of claim 15, further comprising delivering the first electronic model with the first attached notation and the second attached notation to the second computer over the network.

19. The method of claim 15, further comprising editing the second attached notation.

20. The method of claim 15, wherein the second attached notation was added by a dental lab to communicate with a doctor or dental practitioner.

* * * * *